(12) United States Patent
Baur et al.

(10) Patent No.: US 7,675,300 B2
(45) Date of Patent: Mar. 9, 2010

(54) CHARGED PARTICLE BEAM DEVICE PROBE OPERATION

(75) Inventors: Christof Baur, Dallas, TX (US); Robert J. Folaron, Plano, TX (US); Adam Hartman, Dallas, TX (US); Philip C. Foster, Murphy, TX (US); Jay C. Nelson, Grapevine, TX (US); Richard E. Stallcup, II, Little Elm, TX (US)

(73) Assignee: Zyvex Instruments, LLC, Richardson, TX (US)

( * ) Notice: Subject to any disclaimer, the term of this patent is extended or adjusted under 35 U.S.C. 154(b) by 28 days.

(21) Appl. No.: 11/957,835

(22) Filed: Dec. 17, 2007
(Under 37 CFR 1.47)

(65) Prior Publication Data

US 2008/0150557 A1    Jun. 26, 2008

Related U.S. Application Data

(62) Division of application No. 11/064,127, filed on Feb. 23, 2005, now Pat. No. 7,319,336.

(60) Provisional application No. 60/546,840, filed on Feb. 23, 2004.

(51) Int. Cl.
*G01R 31/305* (2006.01)
*G01R 31/02* (2006.01)
*G01R 31/26* (2006.01)

(52) U.S. Cl. .................. 324/751; 324/758; 324/765

(58) Field of Classification Search ............ 324/158.1, 324/750–752, 758, 765; 250/306–311, 397, 250/442.11
See application file for complete search history.

(56) References Cited

U.S. PATENT DOCUMENTS 2,782,682 A    2/1957    Browning et al.

(Continued)

FOREIGN PATENT DOCUMENTS

CN    2158072 Y    3/1994

(Continued)

*Primary Examiner*—Ha Tran T Nguyen
*Assistant Examiner*—Joshua Benitez
(74) *Attorney, Agent, or Firm*—Haynes and Boone LLP

(57) ABSTRACT

An apparatus including a positioner control device, a measuring device and a control routine. The positioner control device is communicatively coupled to a chamber of a charged particle beam device (CPBD) and is configured to individually manipulate each of a plurality of probes within the CPBD chamber to establish contact between ones of the plurality of probes and corresponding ones of a plurality of contact points of a sample positioned in the CPBD chamber. The measuring device is communicatively coupled to the CPBD and the positioner control device and is configured to perform one of a measurement and a detection of a characteristic associated with one of the plurality of contact points. The control routine is configured to at least partially automate control of at least one of the CPBD, the positioner control device and the measuring device.

27 Claims, 13 Drawing Sheets

U.S. PATENT DOCUMENTS

| | | | |
|---|---|---|---|
| 3,119,266 A | 1/1964 | Atkinson | |
| 3,134,942 A | 5/1964 | Rhodes | |
| 3,535,515 A | 10/1970 | Jones et al. | |
| 3,714,423 A | 1/1973 | Lucas | |
| 4,019,073 A | 4/1977 | Vishnevsky et al. | |
| 4,463,257 A | 7/1984 | Simpkins et al. | |
| 4,587,431 A | 5/1986 | Uemura | |
| 4,601,551 A | 7/1986 | Pettingell et al. | |
| 4,607,220 A | 8/1986 | Hollman | |
| 4,610,475 A | 9/1986 | Heiserman | |
| 4,672,256 A | 6/1987 | Okuno et al. | |
| 4,678,955 A | 7/1987 | Toda | |
| 4,729,646 A | 3/1988 | Clark et al. | |
| 4,736,129 A | 4/1988 | Endo et al. | |
| 4,798,989 A | 1/1989 | Miyazaki et al. | |
| 4,850,779 A | 7/1989 | Cashell et al. | |
| 4,874,979 A | 10/1989 | Rapp | |
| 4,880,975 A | 11/1989 | Nishioka et al. | |
| 4,893,914 A | 1/1990 | Hancock et al. | |
| 4,919,001 A | 4/1990 | Ogiwara et al. | |
| 4,956,923 A | 9/1990 | Pettingell et al. | |
| 5,036,205 A | 7/1991 | Clement et al. | |
| 5,055,680 A | 10/1991 | Kesmodel et al. | |
| 5,068,535 A | 11/1991 | Rabalais | |
| 5,081,353 A | 1/1992 | Yamada et al. | |
| 5,089,740 A | 2/1992 | Ono | |
| 5,117,110 A | 5/1992 | Yasutake et al. | |
| 5,124,645 A | 6/1992 | Rhoden et al. | |
| 5,225,683 A | 7/1993 | Suzuki et al. | |
| 5,237,238 A | 8/1993 | Berghaus et al. | |
| 5,270,552 A | 12/1993 | Ohnishi et al. | |
| 5,332,275 A | 7/1994 | Conway et al. | |
| 5,338,997 A | 8/1994 | Benecke | |
| 5,412,503 A | 5/1995 | Nederlof | |
| 5,455,420 A * | 10/1995 | Ho et al. | 850/1 |
| 5,458,387 A | 10/1995 | Conway et al. | |
| 5,493,236 A | 2/1996 | Ishii et al. | |
| 5,510,615 A | 4/1996 | Ho et al. | |
| 5,538,305 A | 7/1996 | Conway et al. | |
| 5,568,004 A | 10/1996 | Kleindiek | |
| 5,589,723 A | 12/1996 | Yoshida et al. | |
| 5,635,836 A | 6/1997 | Kirtley et al. | |
| 5,677,709 A | 10/1997 | Miura et al. | |
| 5,727,915 A | 3/1998 | Suzuki | |
| 5,756,997 A * | 5/1998 | Kley | 850/1 |
| 5,886,684 A | 3/1999 | Miura et al. | |
| 5,895,084 A | 4/1999 | Mauro | |
| 5,922,179 A | 7/1999 | Mitro et al. | |
| 5,939,816 A | 8/1999 | Culp | |
| 5,973,471 A | 10/1999 | Miura et al. | |
| 5,980,950 A | 11/1999 | Porter | |
| 5,989,779 A | 11/1999 | Hatakeyama et al. | |
| 5,994,820 A | 11/1999 | Kleindiek | |
| 5,998,097 A | 12/1999 | Hatakeyama et al. | |
| 6,000,280 A | 12/1999 | Miller et al. | |
| 6,002,136 A | 12/1999 | Naeem | |
| 6,007,696 A | 12/1999 | Takayasu et al. | |
| 6,010,831 A | 1/2000 | Hatakeyama et al. | |
| 6,043,548 A | 3/2000 | Cahen et al. | |
| 6,048,671 A | 4/2000 | Hatakeyama et al. | |
| 6,105,589 A | 8/2000 | Vane | |
| 6,111,336 A | 8/2000 | Yoshida et al. | |
| 6,127,681 A | 10/2000 | Sato et al. | |
| 6,127,682 A | 10/2000 | Nakamoto | |
| 6,188,161 B1 | 2/2001 | Yoshida et al. | |
| 6,191,598 B1 * | 2/2001 | Hollman | 324/758 |
| 6,194,833 B1 | 2/2001 | DeTemple et al. | |
| 6,198,299 B1 | 3/2001 | Hollman | |
| 6,210,988 B1 | 4/2001 | Howe et al. | |
| 6,268,958 B1 | 7/2001 | Furuhashi | |
| 6,279,007 B1 | 8/2001 | Uppala | |
| 6,279,389 B1 | 8/2001 | Adderton et al. | |
| 6,329,826 B1 * | 12/2001 | Shinada et al. | 324/751 |
| 6,337,479 B1 | 1/2002 | Kley | |
| 6,344,750 B1 * | 2/2002 | Lo et al. | 324/751 |
| 6,346,710 B1 | 2/2002 | Ue | |
| 6,353,219 B1 | 3/2002 | Kley | |
| 6,403,968 B1 | 6/2002 | Hazaki et al. | |
| 6,420,722 B2 | 7/2002 | Moore et al. | |
| 6,422,077 B1 | 7/2002 | Krauss et al. | |
| 6,448,622 B1 | 9/2002 | Franke et al. | |
| 6,452,307 B1 | 9/2002 | Olin et al. | |
| 6,452,315 B1 | 9/2002 | Vane | |
| 6,501,289 B1 | 12/2002 | Takekoshi | |
| 6,538,254 B1 | 3/2003 | Tomimatsu et al. | |
| 6,539,519 B1 | 3/2003 | Meeker | |
| 6,576,900 B2 | 6/2003 | Kelly et al. | |
| 6,580,076 B1 | 6/2003 | Miyazaki | |
| 6,583,413 B1 | 6/2003 | Shinada et al. | |
| 6,597,359 B1 | 7/2003 | Lathrop | |
| 6,603,239 B1 | 8/2003 | Michely et al. | |
| 6,610,257 B2 | 8/2003 | Vane | |
| 6,621,282 B2 | 9/2003 | Hollman | |
| 6,627,889 B2 | 9/2003 | Ochiai et al. | |
| 6,664,552 B2 | 12/2003 | Shichi et al. | |
| 6,690,101 B2 | 2/2004 | Magnussen et al. | |
| 6,777,674 B2 | 8/2004 | Moore et al. | |
| 6,781,125 B2 | 8/2004 | Tokuda et al. | |
| 6,841,788 B1 | 1/2005 | Robinson et al. | |
| 6,861,648 B2 | 3/2005 | Kley | |
| 6,865,509 B1 | 3/2005 | Hsiung et al. | |
| 6,891,170 B1 * | 5/2005 | Yu et al. | 250/442.11 |
| 6,927,400 B2 | 8/2005 | Rasmussen | |
| 6,960,765 B2 | 11/2005 | Tomimatsu et al. | |
| 6,967,335 B1 | 11/2005 | Dyer et al. | |
| 6,982,429 B2 | 1/2006 | Robinson et al. | |
| 6,986,739 B2 | 1/2006 | Warren et al. | |
| 7,043,848 B2 | 5/2006 | Hollman | |
| 7,045,780 B2 | 5/2006 | Kley | |
| 7,074,310 B2 | 7/2006 | Smalley et al. | |
| 7,114,406 B2 | 10/2006 | Wright et al. | |
| 2001/0044156 A1 | 11/2001 | Kelly et al. | |
| 2002/0000522 A1 | 1/2002 | Alani | |
| 2002/0027563 A1 | 3/2002 | Van Doan et al. | |
| 2002/0053522 A1 | 5/2002 | Cumings et al. | |
| 2002/0064341 A1 | 5/2002 | Fauver et al. | |
| 2002/0121614 A1 | 9/2002 | Moore | |
| 2002/0125427 A1 | 9/2002 | Chand et al. | |
| 2002/0138353 A1 | 9/2002 | Schreiber et al. | |
| 2002/0166976 A1 | 11/2002 | Sugaya et al. | |
| 2002/0195422 A1 | 12/2002 | Sievers et al. | |
| 2003/0042921 A1 | 3/2003 | Hollman | |
| 2003/0089852 A1 | 5/2003 | Ochiai et al. | |
| 2003/0089860 A1 | 5/2003 | Asjes | |
| 2003/0137539 A1 | 7/2003 | Dees | |
| 2003/0187867 A1 | 10/2003 | Smartt | |
| 2003/0212725 A1 | 11/2003 | Ovshinsky et al. | |
| 2004/0205093 A1 | 10/2004 | Li et al. | |
| 2004/0245466 A1 | 12/2004 | Robinson et al. | |
| 2005/0029467 A1 | 2/2005 | Yu et al. | |
| 2005/0178980 A1 | 8/2005 | Skidmore et al. | |
| 2005/0184028 A1 | 8/2005 | Baur et al. | |
| 2005/0184236 A1 | 8/2005 | Baur et al. | |
| 2005/0193576 A1 | 9/2005 | Hollman et al. | |
| 2006/0076503 A1 | 4/2006 | Tsao | |
| 2006/0180264 A1 | 8/2006 | Kisch et al. | |
| 2006/0192116 A1 | 8/2006 | Baur | |
| 2007/0022804 A1 | 2/2007 | Kley | |

FOREIGN PATENT DOCUMENTS

| | | |
|---|---|---|
| DE | 19524907 A1 | 1/1997 |
| EP | 0927880 | 7/1999 |
| EP | 1516220 | 3/2005 |

| | | |
|---|---|---|
| EP | 1520200 | 4/2005 |
| EP | 1566647 | 8/2005 |
| EP | 1574282 | 9/2005 |
| EP | 1671346 | 6/2006 |
| JP | 2072535 | 3/1990 |
| JP | 5018706 | 1/1993 |
| JP | 11135051 A | 5/1999 |
| JP | 2001198896 A | 7/2001 |
| JP | 2002033366 A | 1/2002 |
| WO | WO96/13724 | 5/1996 |
| WO | WO 96/20495 | 7/1996 |
| WO | WO 00/10191 | 8/1999 |
| WO | 0013030 | 3/2000 |
| WO | WO01/09965 | 2/2001 |
| WO | WO02/16089 | 2/2002 |
| WO | WO03/107066 | 12/2003 |
| WO | WO03/107066 A1 | 12/2003 |
| WO | WO2005/031789 | 5/2005 |
| WO | WO2005/031789 A3 | 5/2005 |

\* cited by examiner

CHARGED PARTICLE BEAM DEVICE PROBE OPERATION

This application is a divisional of U.S. patent application Ser. No. 11/064,127, filed Feb. 23, 2005, which claims the benefit of U.S. Provisional Application No. 60/546,840, entitled "AUTOMATED AND SEMI-AUTOMATED PROBING IN A CHARGED PARTICLE BEAM DEVICE," filed Feb. 23, 2004, the disclosures of both are hereby incorporated herein by reference.

This application is also related to commonly-assigned U.S. application Ser. No. 11/063,692, filed Feb. 23, 2005, entitled "PROBE CURRENT IMAGING," the disclosure of which is hereby incorporated herein by reference.

This application is also related to commonly-assigned U.S. application Ser. No. 11/064,131, filed Feb. 23, 2005, entitled "PROBE TIP PROCESSING," the disclosure of which is hereby incorporated herein by reference.

The present application is also related to: (1) U.S. patent application Ser. No. 10/173,542, filed Jun. 17, 2002, entitled "MANIPULATION SYSTEM FOR MANIPULATING A SAMPLE UNDER STUDY WITH A MICROSCOPE"; (2) U.S. patent application Ser. No. 10/173,543, filed Jun. 17, 2002, entitled "MODULAR MANIPULATION SYSTEM FOR MANIPULATING A SAMPLE UNDER STUDY WITH A MICROSCOPE"; and (3) U.S. patent application Ser. No. 10/948,385, filed Sep. 23, 2004, entitled "METHOD, SYSTEM AND DEVICE FOR MICROSCOPIC EXAMINATION EMPLOYING FIB-PREPARED SAMPLE GRASPING ELEMENT".

BACKGROUND

A charged particle beam device (CPBD) is often required to examine and perform manipulation of micro- and nano-scale objects. In general, a CPBD employs a charged particle beam (CPB) to irradiate a sample under study, or a focused spot on the study, wherein the wavelength of the CPB is much smaller than the wavelength of light used in optical microscopes. Modern CPBD can view details at the atomic level with sub-nanometer resolution (e.g., down to about 0.1 nm resolution) at a magnification of up to about one million. CPB microscopes and others which may be similarly employed include scanning electron microscopes (SEM), focused ion beam (FIB) microscopes and transmission electron microscopes (TEM), among others.

A scanning electron microscope (SEM) is another type of CPB microscope. In an exemplary SEM, a beam of electrons may be focused to a point (e.g., "spot" mode) and scanned over the surface of the specimen. Detectors collect the backscattered and secondary electrons reflected or otherwise originating from the surface of the specimen and convert them into a signal that is used to produce a realistic, multi-dimensional image of the specimen. SEMs can provide a magnification of up to about two hundred thousand, possibly higher.

For some applications, a probe or plurality of probes may be used inside a CPBD to acquire additional data, properties and/or characteristics of samples. Such probes may also be used to performed tests on or with samples within the CPBD to collect such data, properties and/or characteristics of samples, among other purposes.

However, it can be difficult to accurately position and/or orient a probe or sample within an SEM or other CPBD. In fact, it can be difficult to even distinguish between the plurality of probes that may be employed within the CPBD to manipulate the sample. It can also be difficult to verify adequate physical and/or electrical contact between a probe and a contact point on a sample.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
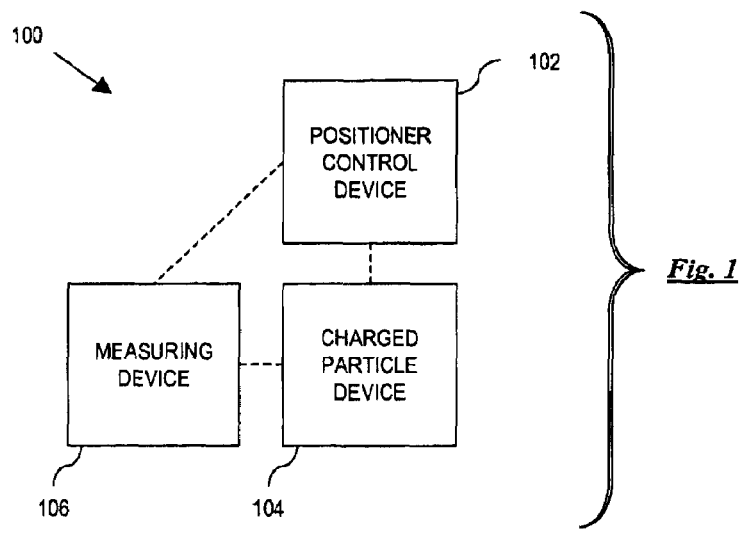
FIG. 1 is a schematic diagram of at least a portion of one embodiment of apparatus according to aspects of the present disclosure.

Disclosed herein are exemplary embodiments of manual, partially automated and substantially automated apparatus and methods for probing one or more samples in a charged particle beam device (CPBD). For example, such probing may comprise or support automated measurement or detection of one or more characteristics of the sample(s). Such characteristics may include mechanical, electrical, optical and/or chemical characteristics, and/or combinations thereof, without limitation. Exemplary samples within the scope of the present disclosure include, without limitation, an integrated circuit (IC), a partially finished IC, a de-processed IC, a transistor, other electronic and micro-electronic devices, micro-electromechanical systems (MEMS) devices, electro-optical devices and circuits, and combinations thereof, among others. Other samples may include nano-particles, nano-materials, coatings, biological samples, and combinations thereof. A CPBD within the scope of the present disclosure may be or include a charged particle beam microscope (CPBM), among others. For example, a CPBM may be or include a focused ion beam (FIB) microscope, a dual-beam FIB microscope, a scanning electron microscope (SEM), a scanning auger microscope (SAM), a transmission electron microscope (TEM), and an environmental scanning electron microscope (ESEM), among others. Of course, the scope of the present disclosure is not limited to the characteristics, samples or CPBDs described above.

Embodiment of methods according to aspects of the present disclosure may include, at least in part, one or more steps or processes for performing the following operations: (1) preparing a sample for introduction into a CPBD; (2) introducing the sample into the CPBD; (3) preparing the sample for measurement using one or more probes; (4) preparing the probes for measurement of one or more characteristics of the sample; (5) locating the probes proximate corresponding target areas on the sample; (6) establishing contact between the probes and the target areas; (7) measuring the characteristic(s); (8) removal of probes and samples from the CPBD; and (9) processing data collected during one or more of the previous processes. Embodiment of methods according to aspects of the present disclosure may also or alternatively include transmitting data collected during one or more of such processes. Such data transmission may be by TCP/IP or other protocols, possibly depending on the transmission destination, wherein possible destinations may include components that are ancillary to, associated with, or merely configured to communicate with the CPBD, including components that are centrally or remotely located relative to the CPBD. One, several or each of such operations, or one or more of the steps or processes executed therefor, may be partially or substantially automated.

Aspects of such automation may be provided by the automation of various devices employed to orient and otherwise operate one or more probes and one or more samples, as well as those devices employed to measure the characteristic(s), all of which may be communicatively coupled as an Automated Probing System (APS). Thus, communications may be sent between these devices to control initiation, adjustment or termination of the above-described operations, or for one or more of the steps or processes executed during such operations. Such communications may also be sent automatically between these devices, such as at the control of the APS and/or otherwise in the absence of user input.

In one embodiment, the APS relies on or otherwise employs a Reference System (RS) by which the orientation of the moving components of the various devices comprising the APS can be referenced to each other and to fixed components or devices. The RS may thus support or provide monitoring of the spatial relationships within the APS, including spatial relationships between and among moving and fixed components or devices. For example, in one embodiment, the spatial relationships of moving components of the various devices is employed to automatically position probe tips relative to each other and/or to features of a sample being probed. Moreover, because the various devices of the APS can be communicatively coupled, information gathered by the RS can be communicated among the devices to initiate, monitor, adjust and/or terminate one or more processes performed by a component or device in the APS, as well as to collect data related to one or more such processes.

The RS and/or other components of the APS, as well as the APS itself, may employ or rely on aspects of U.S. patent application Ser. No. 10/698,178, "SYSTEM AND METHOD OF PROCESSING DAG OCTREE," filed Oct. 31, 2003, and/or U.S. patent application Ser. No. 10/749,256, "ISO-SURFACE EXTRACTION INTO SPLAT HIERARCHY," filed Dec. 31, 2003, each of which are hereby incorporated by reference in their entirety herein. These applications relate to computer simulation and imaging aspects which may be employed to generate and display static and real-time images of probes, samples and CPBD chambers within the scope of the present disclosure. For example, such computer simulated imaging may be employed in support of collision avoidance procedures during the transport of samples and probes within a CPBD chamber according to aspects of the present disclosure. However, such collision avoidance may additionally or alternatively be implemented in a more physical form, such as by proximity and/or contact detection, including in a partially or substantially automated manner.

The RS can comprise a variety of devices such as, without limitation, location sensors, pressure sensors, environmental sensors, material/element sensors, and/or timers, among others. The RS may also include one or more devices operable to execute location procedures, such as locating by imaging. The devices and/or components of the RS may be operable to gather information regarding the various devices and/or components of the APS and/or the steps, processes, actions or operations performed thereby. The RS may also include programming and/or software for converting the gathered information, such as into messages that may be communicated among the devices. For example, the messages from the RS may be in the form of an electronic signal, or may be in the form of a command generated by software associated with the RS.

The RS may be implemented as a part of a Control Routine (CR) that may be programmed into one of the communicatively coupled devices of the APS. In one such embodiment, the RS is implemented in the CR as a set of procedures that are programmed into a position control device that provides operability to the probes. The CR may also comprise various sub-routines for enabling automated probing and other automated processes according to aspects of the present disclosure.

Various aspects of the RS may vary depending on the type of process or processes to be performed by the RS, possibly including automated processes. For example, the information required by the RS during the automated preparation of a probe can vary from the information required by the RS during the automated measurement of a characteristic of a sample. In some embodiments, however, possibly regardless of the type of automated process or processes being performed, the RS relies on certain common factors, such as the position of a sample relative to a charged particle beam (CPB) produced by a CPBD, the position of probe tips relative to the sample, and a map of the sample.

A map of the sample refers to data regarding the sample that can be used, for example, to determine the location of features on the sample. For example, the sample may be a semiconductor chip with certain features formed thereon. A map of the chip may provide location information regarding one or more of those features. A map of a sample can be obtained from a variety of sources including, for example, computer-aided design (CAD) data, manual training of the sample by a user, and/or a set of reference coordinates specified by a user and/or an external system.

In embodiments in which the RS relies on the position of a sample relative to a CPB, the RS may use information obtained from a process implemented by the CR for determining the position of the sample positioned in a sample chamber of the CPBD relative to the CPB. Alternatively, or additionally, the CR may include one or more processes employable to determine the location of the sample relative to a positioning stage or probe tip, as well as one or more processes employable to determine the location of the stage or probe tip relative to the CPB. Alternatively, or additionally, the CR may include one or more processes employable to determine the location of the probe tip relative to the positioning stage, as well as one or more processes employable to determine the location of the stage relative to the CPB.

In one embodiment, the CR implements a standard image-analysis procedure to determine the position of the sample relative to the CPB, the positioning stage and/or the probe tip. For example, the image can be derived from a representation created from the CPBD or other such device that can create a suitable representation for use by image-analysis software. Reference features on the sample, stage and/or probe tip can be used in the image-analysis to create a mathematical coordinate system to describe the location of the sample, stage and/or probe tip to the RS.

In embodiments in which the RS relies on the position of the probe tips relative to the sample, the RS may use information obtained from a process implemented by the CR for determining the location of the probe tips relative to the position of the sample in the sample chamber. For example, the location of the probe tips relative to the CPB and/or stage may be determined using suitable image-analysis techniques. Alternatively, or additionally, the location of the probe tips relative to the probe positioner may be determined, and then the location of the probe tips relative to the CPB or stage may be determined. The location of the probe tips can be determined by image-analysis, or by moving the probe tips to a mechanical, electrical or laser sensor that provides suitable feedback for such a requirement, among other possible methods.

In embodiments in which the RS relies on a map, the RS may communicate information to a device providing operability of the probes, such as a positioner control device, which may trigger such device to drive the position of the probe tips over specified features. For example, the coordinates of features relative to the map and the actual location of the sample under inspection, or the actual location of the probe tips, and/or the actual location of the positioners can be mathematically combined.

Referring to FIG. 1, illustrated is at least a portion of one embodiment of an apparatus 100 according to aspects of the present disclosure. The apparatus 100 may include or be substantially similar to an APS according to one or more of the aspects described above.

The apparatus 100 includes a positioner control device 102, a CPBD 104 and a measuring device 106. The positioner control device 102 may be configured to control a manipulation platform to which one or more probes are coupled. For example, the positioner control device 102 may be or include the S100 Nanomanipulator System commercially available from Zyvex Corporation, among other manipulators. The CPBD 104 may be or include an SEM or FIB available from FEI, Hitachi or JEOL, among others. The measuring device 106 may be or include the Keithley 4200, which is also commercially available, among other measuring devices.

The positioner control device 102, the CPBD 104 and the measuring device 106 are coupled such that communications are sent between the devices to initiate, adjust, monitor, collect data relative to, and/or terminate processes. Such processes may include introducing a sample into a the CPBD 104, preparing a plurality of probes for taking a measurement of the sample, locating the probes proximate a target area on the sample, activating the probes to make contact with the target area, and/or taking the measurement, among others. The communications among the devices may be interpreted by the CR which, as described above, may be programmed into one or more of the devices of the apparatus 100. Consequently, the CR may instruct the devices of the apparatus 100 to initiate, monitor, collect data related to, adjust and/or terminate a particular process, such as preparing the probes or taking measurements, in response to communications received from the CPBD 104 and/or the measuring device 106.

The CR may be programmed into a single computer or machine (e.g., a "master control computer") that is responsible for directing the operation of one or more of the positioner control device 102, the CPBD 104 and the measuring device 106, at least in part, and may also be responsible for controlling one or more of the steps, processes, actions and/or operations described above. For example, a procedure for introducing a sample into the CPBD 104 may be controlled by the same computer that operates the positioner control device 102 and that drives probes to a desired location, and/or by the same computer that controls peripheral devices. In addition, Data Acquisition (DA) boards and other DA devices may be implemented in the computer or machine operating the positioner control device 102, for example, to enable the positioner control device 102 to take measurements that would otherwise be implemented by a computer, machine or operation system of the measuring device 106. In embodiments in which the CR and operation of one or all of the devices of the apparatus 100 or APS reside on a single machine, communication among the various devices may be enabled via software. In other embodiments, one or more of the positioner control device 102, the CPBD 104 and the measuring device 106 may comprise or be associated with a separate computer or machine to direct operation. In such embodiments, each device may be communicatively coupled by pathways such as wire, cable, network (e.g., TCP/IP network over Ethernet, 1394 connection, and/or USB, among others), or wireless protocol, among other means. Thus, communications between the devices of the apparatus 100 may be implemented as logical operations and/or subsystems that are accessed via a separate computer via a physical network, or may reside locally to a master control computer or other singular or plural computing device.

Figure 2:
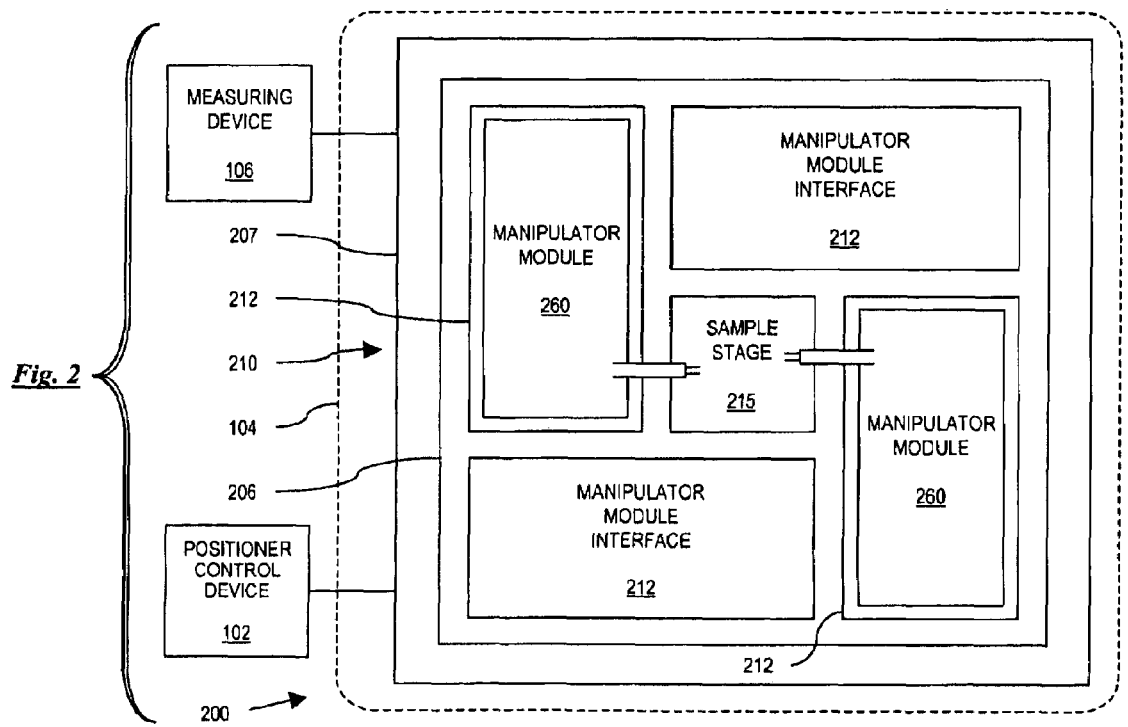
FIG. 2 is a block diagram of at least a portion of one embodiment of apparatus according to aspects of the present disclosure.

Referring to FIG. 2, illustrated is a block diagram of at least a portion of one embodiment of an apparatus 200 according to aspects of the present disclosure. The apparatus 200 is one environment by which messages communicated between the devices of the apparatus 100 may be implemented. The apparatus 200 may be configured to fit within the chamber of the CPBD 104, including configurations in which components of the apparatus 200 are in communication with the positioner control device 102 and/or the measuring device 106, whether the positioner control device 102 and/or the measuring device 106 are also disposed within the CPBD 104 chamber or are external to the CPBD 104 chamber. The apparatus 200 may also include one or more of the CPBD 104, the positioner control device 102 and the measuring device 106. However, in the illustrated embodiment, the apparatus 200 is a discrete component or subassembly positioned within the chamber of the CPBD 104 and communicatively coupled to the CPBD 104, the positioner control device 102 and the measuring device 106.

The apparatus 200 includes a manipulation platform 210 for manipulating one or more samples within the CPBD 104. Manipulation of a sample may include, without limitation, moving a sample in X, Y, Z, DX, DY and DZ directions. Manipulation of a sample may additionally or alternatively include the determination of physical and chemical characteristics of a sample, such as performing electrical, mechanical, optical, or chemical measurements, or combinations thereof. In one embodiment, the apparatus 200 includes a plurality of manipulation platforms 210, whether substantially similar or having varying configurations. The manipulation platform 210 may also be reconfigurable, such as may allow the custom alteration of the layout and/or functionality described below.

The manipulation platform 210 includes at least one base 206 on which a plurality of manipulator module interfaces 212 are arranged. Each of the manipulator module interfaces 212 are configured to receive a manipulator module 260. In the illustrated embodiment, the manipulation platform 210 includes four manipulator module interfaces 212, and manipulator modules 260 are coupled to two of the manipulator module interfaces 212. However, other embodiments within the scope of the present disclosure may include a different number of manipulator module interfaces 212 and/or manipulator modules 260. Moreover, each manipulator module interface 212 need not be identical to the other manipulator module interfaces 212, and each manipulator module 260 need not be identical to the other manipulator modules 260.

The manipulator platform 210 also includes a sample stage 215 configured to receive one or more samples to be manipulated within the CPBD 104. The sample stage 215 may alternatively be a discrete component coupled to the manipulator platform 210 by mechanical fasteners, adhesive, or other means. The manipulator platform 210 may also include a plurality of sample stages 215 each configured to receive one or more samples to be manipulated within the CPBD 104.

The manipulator platform 210 also includes or is associated with an interface 207 that is configured to couple the base 206 to an SEM or other device employed as the CPBD 104 in FIG. 2. The interface 207 may be integral to the manipulator platform 210, or may be a discrete component coupled to the base 206 by mechanical fasteners, adhesive, or other means. The interface 207 may be or include a mechanical interface, an electrical interface, a combined mechanical/electrical interface, or separate mechanical and electrical interfaces, among others. Thus, for example, in an embodiment in which an SEM is employed as the CPBD 104 to which the base 206 is coupled via the interface 207, a sample may be arranged on sample stage 215 and the manipulation platform 210 may be positioned within the sample chamber of the SEM by way of an electrical and/or mechanical coupling to the SEM via the interface 207. Consequently, once the platform 210 is coupled to an SEM (or other CPBD 104), a sample arranged on the sample stage 215 may be imaged substantially simultaneously with the manipulation of the sample via the manipulator modules 260.

As also depicted in the embodiment illustrated in FIG. 2, a positioner control device 102 may be coupled to the manipulation platform 210 via the interface 207. Consequently, the CPBD 104 and the positioner control device 102 may be communicatively coupled such that communications may be sent between the CPBD 104 and the positioner control device 102, as well as communications with sensors located within these devices and configured to derive information for use in the RS, for example.

The positioner control device 102 may be programmed for automated control of the operation of manipulator modules 260 via the manipulator module interfaces 212. Thus, a CR as described above, which may include the RS as a set of methods, may also be programmed into the positioner control device 102 to instruct the devices making up the apparatus 200 (and/or the apparatus 100 of FIG. 1) to initiate, monitor, adjust or terminate one or more steps, process, actions or operations, and/or to collect data related thereto. For example, in response to communications received from the CPBD 104 and/or the measuring device 106, the CR and/or another function or feature of the positioner control device 102 may automate the initiation, monitoring adjustment, termination, and/or data collection related to preparing probes, preparing a sample, imaging a sample or taking a measurement.

The embodiment shown in FIG. 2 also demonstrates that the measuring device 106 may be mechanically and/or electrically coupled to the manipulation platform 210. The measuring device 106 may be programmed for automated control of the measurement or detection of characteristics of a sample arranged on the stage 215. The coupling between the measuring device 106 and the manipulation platform 210 may enable communication between the measuring device 106 and the positioner control device 102. Thus, in one embodiment, the measuring device 106, the positioner control device 102 and the CPBD 104 are collectively coupled, each to the other two, thereby at least partially composing an APS as described above. As also described above, a CR comprising an RS configured to reference fixed and/or moving components of the measuring device 106, the positioner control device 102 and the CPBD 104, including relative movement of such components, can be programmed into one or more of the measuring device 106, the positioner control device 102 and the CPBD 104. Consequently, signals generated by the RS can be communicated by and through the communicative couplings between the measuring device 106, the positioner control device 102 and the CPBD 104.

The positioner control device 102 may comprise any suitable processor-based system, such as a personal computer (PC), that may be configured to control the operation of one or more components of the apparatus 200. For example, the positioner control device 102 may communicate command signals (e.g., electrical signals) to the manipulator modules 260 via the manipulator module interfaces 212 to control the operation of the manipulator modules 260. Such communication may be via one or more conductive traces and/or other types of communication paths, such as those that may be extend along one or more surfaces of the manipulator platform 210 to the manipulator module interfaces 212.

The positioner control device 102 may also include software executable to control components of the apparatus 200. For example, software executed by positioner control device 102 may generate and/or communicate command signals to one or more of the manipulator modules 260 via the manipulator module interfaces 212, possibly in an automated fashion and/or responsive to user input received by the positioner control device 102, the measuring device 106, and/or the CR. Such signals may also be generated and/or communicated in response to feedback or other communications received from the manipulator module interfaces 212 and/or the manipulator modules 260, and/or to communications received by the positioner control device 102 from the CPBD 104.

In one embodiment, the manipulator modules 260 include logic for communicating their individual operative capabilities to the positioner control device 102. For example, a manipulator module 260 may comprise logic for transmitting information about its movement capabilities, such as whether it is configured to generate translational movement in one or more orthogonal dimensions, whether it can generate rotational movement about one or more orthogonal axes, its current orientation, and/or other information. The manipulator modules 260 may also include logic for communicating information about its end-effector and the type of probes assembled therein, where such information may again be communicated with the positioner control device 102, among other components of the apparatus 200.

The manipulator modules 260 each couple to or otherwise interface with a corresponding manipulator module interface 212 on the platform 210. For example, each manipulator module 260 may include a communication interface (e.g., an electrical input and/or output interface) configured to couple with the communication path of one or each of the manipulator module interfaces 212. In one embodiment, such a communication interface or other portion of the manipulator modules 260 may include conductive traces for receiving input signals for controlling operation. Accordingly, coupling a manipulator module 260 to manipulator module interface 212 can include contacting or otherwise coupling the conductive traces on each of the manipulator module 260 and the manipulator module interface 212.

The manipulator modules 260 may also include or be associated with motion and/or displacement sensors. Signals from such sensors can also be routed into the positioner control device 102. Consequently, the positioner control device 300 may be implemented with control software and/or hardware configured to monitor the position or orientation of a manipulator module 260 in real-time, as well as possibly calibrating or correcting the orientation. The positioner control device 102 may also include or be coupled to an imaging system, such as may be provided by or associated with the CPBD 104, and may thus perform or support real-time object recognition and positioning identification which may be employed to control the orientation of the manipulator modules 260 and/or end-effectors of the manipulator modules 260, possibly in an automated manner.

At least with regard to some embodiments of automated processes that are described herein, the CR may be programmed or otherwise configured to recognize conditions that may require human intervention. In such embodiments, human intervention can be accommodated via a user interface suitable to such intervention. Additionally, or alternatively, the CR may be configured for initiation by a higher level control routine, as well as communication of system and/or process data with the higher level control routine.

Figure 3A:
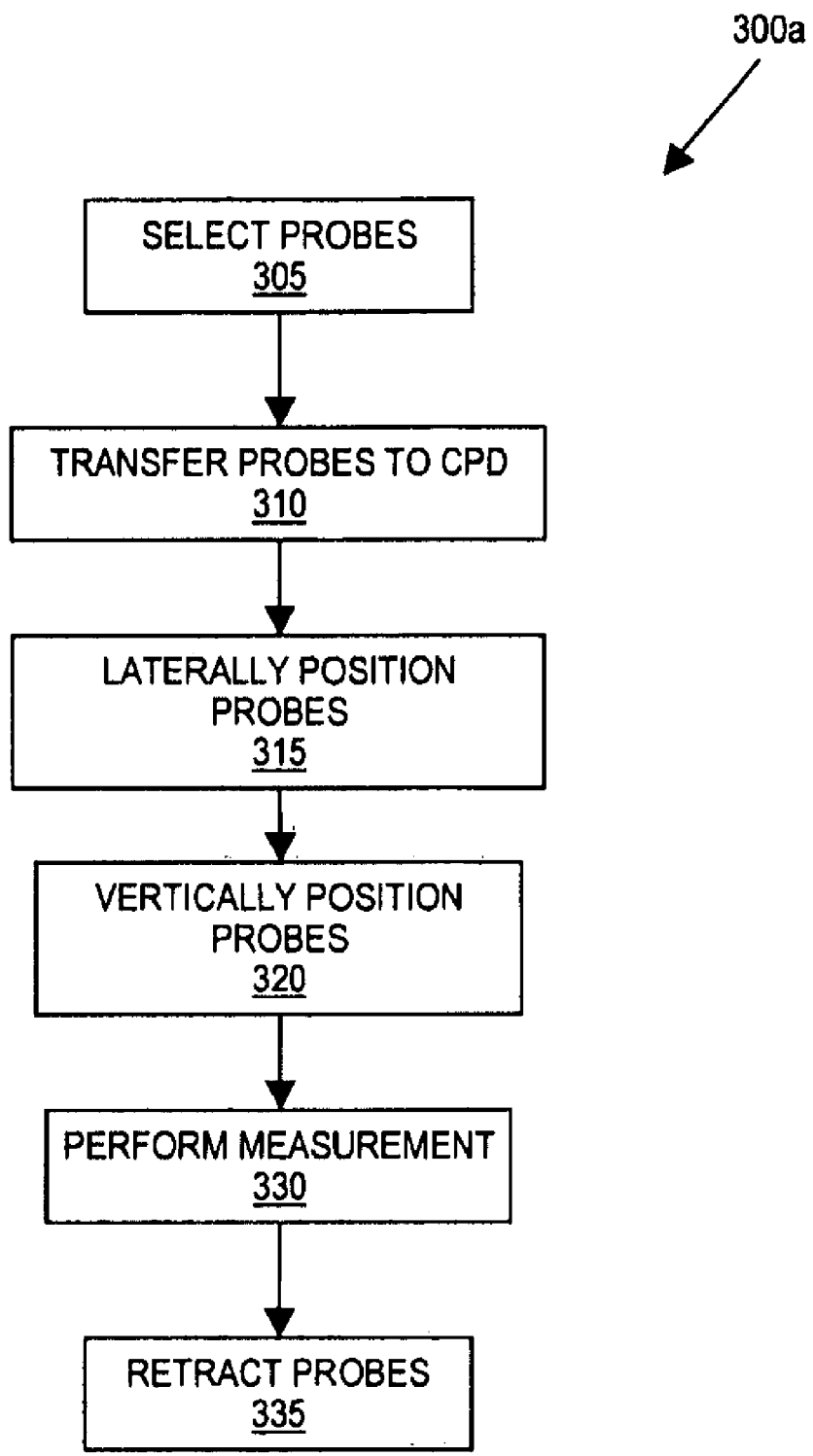
FIG. 3A is a flow-chart diagram of at least a portion of one embodiment of a method according to aspects of the present disclosure.

Referring to FIG. 3A, illustrated is a flow-chart diagram of at least a portion of one embodiment of a method 300*a* according to aspects of the present disclosure. The method 300*a* may be performed or executed by the apparatus 100 of FIG. 1 and/or the apparatus 200 of FIG. 2, among other apparatus according to aspects of the present disclosure. Moreover, one or more portions of the method 300*a* may be performed or executed in a substantially automated manner. In one embodiment, the method 300*a* is substantially automated.

Additionally, aspects of the method 300*a* and other methods within the scope of the present disclosure are applicable to single probe and multiple probe applications. Thus, for the sake of simplicity and clarity, any reference herein to a plurality of probes or a multiple probe method, process or application is also applicable to a single probe or a single probe method, process or application. Also, each of the processes, procedures, actions and operations described below as composing one or more embodiments of the method 300*a*, as well as other methods within the scope of the present disclosure, may independently include multiple processes, procedures, actions and/or operations.

The method 300*a* may include a probe selection step or process 305 by which one or more probes are selected based on a characteristic to be measured or detected. The probes may alternatively, or additionally, be selected based on the manner of measuring or detecting the characteristic. For example, probes suitable for measuring an electrical characteristic of a sample may include, without limitation, probes substantially comprising tungsten, platinum or gold wire, or probes having probe tips of such composition.

The selection of one or more probes by or during the process 305 may be manual, partially automated or substantially automated. For example, manual embodiments of the process 305 may substantially rely on user input. Partially automated embodiments of the process 305 may automatically perform a subset of the actions and/or decisions of the process 305. Automated aspects of partially automated embodiments may include process initiation, process performance, process monitoring and/or adjustment (e.g., time, power, speed, force, etc.), process termination, and/or process errors, among others. Substantially automated embodiments of the process 305 may substantially rely on automated robotics and/or other machinery or apparatus, and/or substantially automated computing hardware and/or software, such that the selection of probes during process 305 may be performed in the substantial absence of user input. This convention, where the extent of automation may substantially be inversely proportional to the amount of user input required or employed during a particular method or method component, or a particular apparatus or function thereof, is also applicable to other aspects of the method 300*a*, as well as to aspects of other methods and apparatus within the scope of the present disclosure.

The method 300*a* also includes a process 310 by which one or more selected probes are introduced into the chamber of a CPBD. In one embodiment, the process 310 may be at least partially automated, such that the probes may be introduced in the CPBD chamber with little or no user input regarding the particulars of, for example, the orientations or locations of the probes within the chamber. However, the process 310 may alternatively be substantially manual or substantially automated. Introducing the probes into the CPBD chamber may also include removing the probes from probe storage structure or locations, whether external or internal to the chamber of the CPBD or other portion of any device, system or other apparatus employed with or including the CPBD.

A process 315 of the method 300*a* includes positioning the tips of the probes above contact points of a sample located in the CPBD chamber. Such positioning may be substantially manual, partially automated or substantially automated. In one embodiment, the positioning may substantially comprise horizontal positioning, such as in a plane that is substantially parallel to a surface of a sample or a platform supporting the sample within the CPBD, or in a plane that is substantially perpendicular to a charged particle beam (CPB) generated within the CPBD. Consequently, subsequent vertical positioning of the probe or probe tips may be in a plane that is substantially perpendicular to the plane of horizontal positioning. Additionally, although many aspects described herein regarding positioning probes or probe tips are described with respect to motion of the probes or tips relative to a stationary sample, such positioning may also include motion of the sample (or the stage or platform supporting the sample) relative to a stationary position of the probes or probe tips, as well as motion of both the sample and the probes or probe tips.

The positioning of the probe tips according to aspects of the method 300a (whether positioning horizontally, vertically or otherwise) may employ the RS, which is configured to positionally reference moving and stationary components relative to one another and/or to a common coordinate system, as described above. Thus, information regarding the location and/or orientation of the probe and/or the probe tips (relative to the sample, manipulators installed within the CPBD chamber, and/or a map of the sample, for example) may be used by the RS to provide appropriate messages to the CR. Consequently, the CR may communicate appropriate messages to a positioner control device (e.g., the positioner controller device 102 of FIGS. 1 and 2) to accurately position the probes above the contact points of the sample. However, in some embodiments, the precision with which the probes or probe tips are positioned over the contact points of the sample may be decreased, such as when contact between the probe tips and the contact points may not be necessary, possibly due to the availability of positioning apparatus and/or methods other than those described with regard to the process 315.

The CR may include one or more probe positioning sub-routines that monitor and/or detect the location and/or orientation of the probes relative to contact points on the sample, which may be registered by the RS. The probe positioning sub-routines may also include procedures for determining when a probe has reached a desired location above a contact point. Exemplary procedures for probe positioning and determining when the probe has reached the desired location include, without limitation, image processing associated with the CPBD, employing the CPB to locate alignment marks of the sample and/or underlying platform, referencing map data obtained by the RS, operating the CPBD in a teaching mode, referencing absolute coordinates on the sample (such as a list of coordinates previously determined), and executing an automated or semi-automated "point and click" process.

A process 320 of the method 300a includes establishing physical and electrical contact between the probes and the contact points on the sample, such as by vertically translating the probes towards the sample via the positioner control device. The probe positioning of the process 320 may be substantially manual, partially automated or substantially automated. When more than one probe is being used, the probes may be lowered simultaneously, in groups, or one at a time, depending on the programming of the positioner control device, for example. In one embodiment, the CR includes a procedure to maintain contact between the probes and the sample until one or more measurement or detection processes are completed. For example, upon contact between a probe tip and a contact point on the sample, a signal may be automatically generated and transmitted to the positioner control device, which may activate a sub-routine of the CR. The activated sub-routine may include an automated process for determining the quality of the contact made with the sample, among other processes.

One or more sample characteristics are measured or detected in a process 330 of the method 300a, wherein the process 330 may be substantially manual, partially automated or substantially automated. The above-described CR may activate a measuring device to perform the measurement or detection, possibly upon receiving communications that confirm physical and/or electrical contact between the probe tips and contact points. The measuring device may be substantially similar to the measuring device 500 shown in FIGS. 1 and 2.

In some embodiments, the measuring device may be a commercially available device, and may include software and/or hardware for performing or supporting the measurement or detection of sample characteristics. The measuring device employed in the process 330 of the method 300a may also have substantially similar aspects to measuring devices described in U.S. Pat. No. 6,208,151, the entire disclosure of which is incorporated herein by reference.

Although the embodiment shown in FIG. 3A depicts the method 300a in a flowchart format, such format should not be interpreted to require that the depicted components of the method 300a occur in series. For example, more than one of the depicted components of the method 300a can also be performed simultaneously. One such example entails preparing one or more probes while employing another one or more probes to measure or detect characteristics of a sample, wherein such probe preparation may be performed in-situ and/or ex-situ of the CPBD chamber in which the sample is being examined. The sequence of the components of the method 300a may also vary from the sequence depicted in FIG. 3A. Moreover, one or more components of the method 300a may be repeated or eliminated yet remain within the scope of the present disclosure.

Figure 3B:
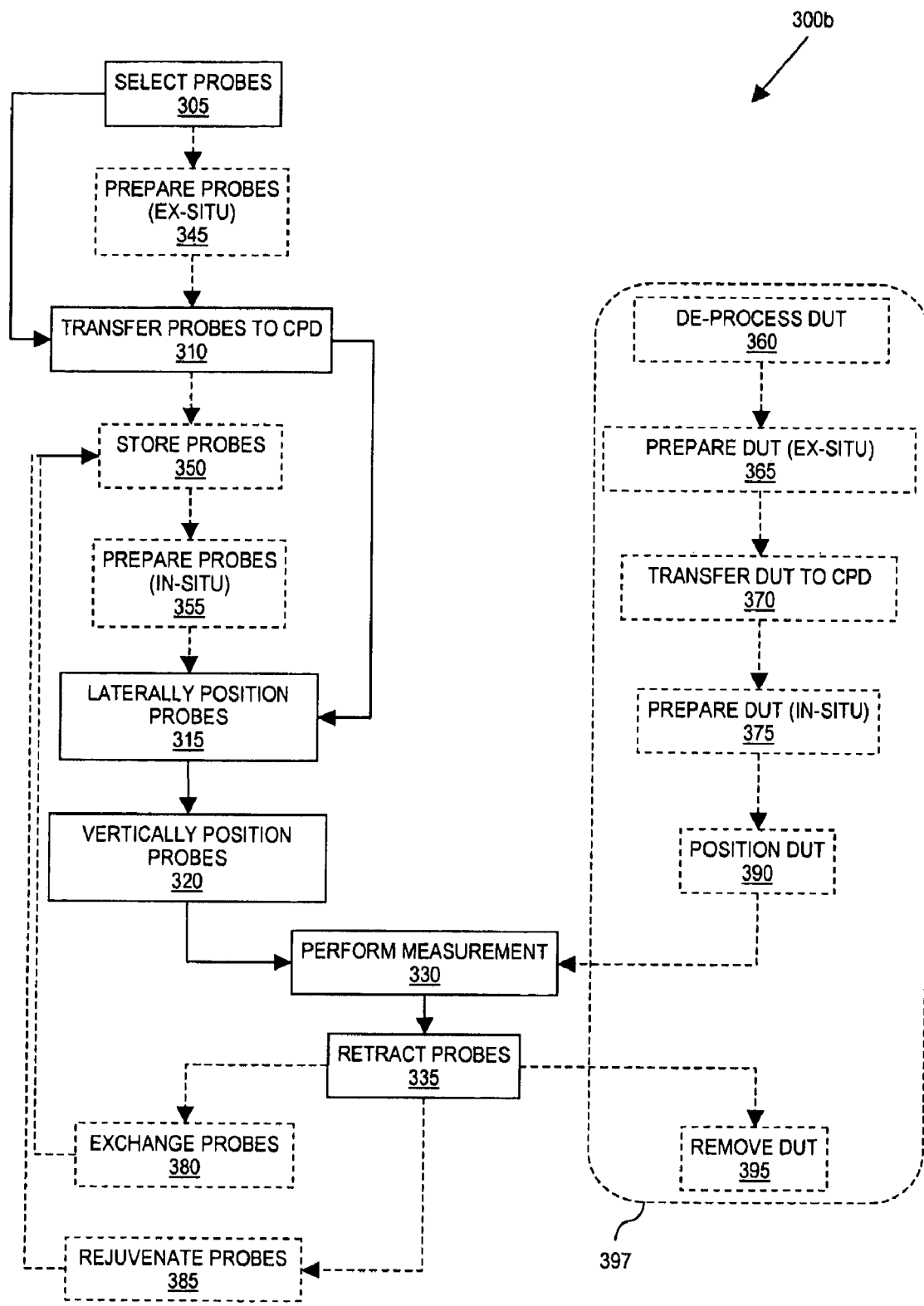
FIG. 3B is a flow-chart diagram of at least a portion of another embodiment of the method shown in FIG. 3A.

Referring to FIG. 3B, illustrated is at least a portion of another embodiment of the method 300a shown in FIG. 3A, herein designated by reference numeral 300b. Embodiments of the method 300b may include one or more of the components of the method 300a. For example, the illustrated embodiment of the method 300b includes each of the components of the method 300a shown in FIG. 3A, as well as one or more additional components. Thus, the following description of the method 300b is substantially directed towards those components which were not explicitly described with regard to the method 300a, although merely for the sake of simplicity and brevity, and without limiting the scope of either method 300a or method 300b within the scope of the present disclosure. Of course, embodiments of the method 300a within the scope of the present disclosure may also include one or more of the components of the method 300b shown in FIG. 3B.

The method 300b may include a process 345 by which ex-situ preparation of one or more probes may optionally be performed. Consequently, the process 345 is depicted in FIG. 3B by dashed lines, in contrast to solid lines. This convention, in which optional processes, steps, actions and/or operations are depicted in dashed lines, as well as the directional indications (arrows) depicting the sequence of such components, is hereafter followed merely for the sake of clarity. Moreover, the depiction of any method, method component or sequence indicator by solid lines, in contrast to dashed lines, does not imply the necessity of such method, component or sequence in any particular embodiment, or otherwise limit the scope of the present disclosure to only those methods that include each aspect depicted by solid lines. To the contrary, any aspect depicted by solid lines or dashed lines in FIGS. 3A and 3B, or any other figure of the present disclosure, may be optional in one or more of the myriad apparatus and methods within the scope of the present disclosure.

The probe preparation performed by the process 345 may include the preparation, conditioning and/or characterization of one or more probes, as described above. However, as also described above, such preparation, conditioning and/or characterization may be collectively referred to herein as "preparation." Nonetheless, some methods within the scope of the present disclosure may not include preparation, conditioning and characterization of one or more probes, but may specifically include only: (1) preparation; (2) conditioning; (3) characterization; (4) preparation and conditioning; (5) preparation and characterization; or (6) conditioning and characterization; where preparation may include one or more processes exclusive of conditioning and characterization. Also, as described above, aspects described herein as applicable to a single probe may also be applicable to multiple probes, aspects described herein as applicable to multiple probes may also be applicable to a single probe, and the same hold true for single and multiple probe tips.

The process 345 may be an ex-situ process in the sense that the probes being prepared by the process 345 undergo such preparation at a location outside of the chamber of the CPBD in which the probes are to be employed to measure or detect a characteristic of a sample oriented in the CPBD. Ex-situ preparation of the process 345 may include one or more processes for determining whether the characteristics of a selected probe are appropriate for the desired measurement or detection for which the probe is to be employed. Additionally, or alternatively, the ex-situ preparation of the process 345 may include one or more processes for effecting remedial measures (e.g., additional or optional probe preparation) if the characteristics of the probe are not appropriate for the intended measurement or detection.

For example, oxide or other contamination that may hinder the utility of a probe as a measuring device may form on the probe tip prior to introducing the probe into the CPBD chamber. Consequently, the ex-situ preparation of the process 345 may include one or more chemical dip processes that may remove or reduce such contamination. Such processes may include one or more hydrofluoric acid or potassium hydroxide dip processes, among others. The ex-situ preparation of the process 345 may also or alternatively include one or more process to sharpen the tip of a probe, such as to improve utility when employing the probe to measure a characteristic of a sample. However, the method 300b may not include the process 345, such as when a selected probe is adequately prepared without requiring ex-situ preparation, possibly including embodiments in which the above-described probe preparation is performed in-situ once the probes have been introduced into the CPBD chamber. Nonetheless, in embodiments including the ex-situ probe preparation of the process 345, such preparation may be substantially manual, partially automated or substantially automated.

The ex-situ preparation of the process 345 may also include sharpening, bending, shaping or other mechanical processing of one or more probes. Such mechanical processing may affect the entire probe or merely a portion of the probe, such as the probe tip, stem or body, for example. In one embodiment, the mechanical processing includes bending the probe to facilitate a dip process, such as one or more of those described above. For example, some probes may be manufactured from wire material stock and, thus, have a substantially cylindrical shape, wherein the mechanical bending process may place one or bends or turns in probe. In one embodiment, only one bend may be formed, such that the resulting probe has a substantially L-shaped profile, although the bend may not be substantially 90 degrees (e.g., the bend may be about 30 degrees in some embodiments, 45 degrees in other embodiments, and 60 degrees in other embodiments). In embodiments in which the probe is bent to include more than one turn, the bent probe may have a zigzag profile, a Z-shaped, or otherwise. Moreover, where probes are mechanically processed to include more than one bend, the bends may be in different planes. For example, a first bend may be in a first plane and a second bend may be in a second plane, where the first and second planes are not coincident, and possibly not parallel.

In embodiments in which ex-situ probe preparation of the process 345 is performed, the CR may implement procedures for the probe preparation as a set of procedures by which the selected preparation process or processes may be monitored by sensors, or by duration of such processing, among other possibilities within the scope of the present disclosure. In one embodiment, the progress and/or completion of one or more probe preparation processes may be monitored or determined by imaging, such as via communication of an appropriate termination signal when the ex-situ preparation is complete.

The method 300b may also include a process 350 by which one or more selected probes are stored in the chamber of the CPBD. The process 350 may be substantially manual or partially automated. However, in one embodiment, the process 350 is substantially automated, such that the probes may be stored in the CPBD chamber with little or no user input regarding the particulars of, for example, the storage orientations or locations of the probes within the chamber.

The method 300b may also include an in-situ process 355 by which one or more probes may undergo probe preparation while located inside the chamber of the CPBD. The in-situ probe preparation of the process 355 may be substantially manual or partially automated. However, the in-situ probe preparation of the process 355 may also be substantially automated, possibly by employing an automated probe preparation system (APPS). The APPS may also be referred to herein or elsewhere as an automated probe conditioning system and/or an automated probe characterizing system. In one embodiment, the APPS may be implemented as a part of the CR described above, such that the APPS also described above may be operable to prepare one or more probes via an automated process.

Embodiments of the above-described APPS may comprise one or more sensors, electrodes or counter electrodes, which may be operable to sense the presence of a probe (e.g., in the CPBD chamber) such that the sensor, electrode or other component of the APPS can subsequently be positioned proximate the probe. Alternatively, or additionally, the probe may be positioned proximate the sensor or other component of the APPS. The proximity of the probe and the APPS component may be about five cm or less, but may also include actual contact between the tip and the APPS component, depending on the type of probe preparation to be performed. When the desired proximity has been reached, the sensor or other APPS component may communicate a signal to the CR indicating such, which the RS may use to register the location of the probe tip (e.g., as located at an absolute location or a location relative to a coordinate system of the RS).

When a probe tip location has been registered, the CR may automatically initiate a selected sub-routine, which may be or include a process for probe preparation. The process selected for initiation by the CR, whether automated or not, may depend upon CR programming.

In embodiments in which the selected process includes probe characterization, the tip diameter, probe material and probe geometry may be measured and/or detected, among other possible physical and/or chemical properties of the probe and the probe tip. Such properties may be examined by one or more processes which may include, without limitation, field emission measurements, visual observation (e.g., with an SEM), energy dispersive x-ray spectroscopy (EDX), and scanning auger mapping. Implementation of these and other probe characterization processes may be controlled by instructions (such as sub-routines) that are provided as a part of the CR. Thus, the CR may be configured to initiate such processes, monitor their progress, and implement appropriate termination commands for the processes, among other actions.

In embodiments in which the selected process includes probe conditioning, instructions (such as sub-routines) for implementing various conditioning procedures may be programmed as a part of the CR. Thus, the CR may also or alternatively be configured to initiate such processes, monitor their progress, and implement appropriate termination commands for the processes. Probe conditioning processes which may be selected can include decontaminating the probe or probe tip and/or sharpening the probe tip, among others. In one embodiment, the CR may be configured to implement a timer which may be employed in association with the initiation and/or termination of one or more probe conditioning procedures. A loop may also be provided within the CR such that one or more conditioning procedures may be repeated for one or more probes until an improved, desired or threshold level of conditioning is achieved. The selection of the one or more probe conditioning procedure(s) may depend on which property of the probe tip requires improvement, at least in part.

In one embodiment, the APPS may be implemented in the CR as a sub-routine to provide commands for performing one or more of the following: (1) pulsing; (2) heating with, for example, e-beam, separate filament, laser, or electron bombardment; (3) field emission; (4) field ionization; (5) field evaporation; (6) field surface melting; (7) ion bombardment/ion milling/ion sputtering; (8); in-situ metal deposition; (9) metal dipping; (10) mechanical deformation of the tip; and (10) an electric charge forced dynamic hot metal flow tip formation (a process referred to hereafter as electric tip processing, or ETP).

Pulsing employed during probe conditioning may comprise contacting the tips to drive current through the probe to remove contamination from the tip. Heating employed during probe conditioning may include heating by electron bombardment, wherein free electrons are generated by a heated filament and accelerated by an electric field to collide with the probe tip, thereby heating the tip by conversion of kinetic energy to thermal energy. This and/or other methods of heating a probe tip may be employed during probe preparation (e.g., probe conditioning) to desorb oxides and adsorbates, thereby cleaning the tip.

Field emission processes which may be employed for probe preparation may include operating a field emission at a high current, which leads to changes of the tip geometry, thereby conditioning the probe tip. Field ionization processes which may be employed for probe preparation may include cleaning the probe tip by applying a high energy field to ionize atoms on the tip. In-situ metal deposition processes which may be employed for probe preparation may include sputtering a metal on the probe tip. Metal dipping processes which may be employed for probe preparation may include dipping at least the tip portion of the probe into a molten source of metal. Mechanical deformation processes which may be employed for probe preparation may include pulling or forging bulk metal and/or other materials to make a sharp probe tip.

ETP may be employed to clean and/or sharpen a probe or probe tip in a non-oxidizing environment using electric current, electric field, and thermal mobilization of atoms, such as metal atoms where the probe or probe tip has a substantially metallic composition. One embodiment of ETP which may be employed to clean and sharpen a probe tip includes bringing a dull probe (to be sharpened) and a thin probe into close proximity. Thereafter, the probes are biased at different voltages such that any oxide or other dielectric or contaminant that is interposing the two probe tips breaks down. For example, the bias differential across the probe tips may be about equal to or greater than the breakdown voltage of the oxide, air or other material interposing the probe tips, such that current flow may be established between the two probes. Such oxide may have been previously formed or allowed to form, or may have undesirably formed, and its existence may have been previously confirmed or merely suspected. In one embodiment, the probes are biased to a relative differential of about 70 volts.

The resulting current between the two probe tips can be sufficient to cause local melting of the thinner probe tip. As the thinner probe tip melts, or as the atoms of the metal become substantially mobile, the electric field driving the electric current between the two probes causes the melted metal of the thinner probe to be accelerated towards the larger probe. If this occurs rapidly enough, the majority of the melted metal may deposit onto the larger probe, while the material at the core of the thinner probe may substantially remain in a solid phase. The transfer of metal from the thinner probe to the larger probe can form a gap between the two probe tips, wherein growth of the gap during ongoing metal transfer from the thinner probe to the thicker probe can be allowed to continue until the gap creates sufficient separation between the probe tips to terminate the electric current established by the voltage differential. ETP can, in some embodiments, clean and/or sharpen the thinner probe.

ETP may be performed either ex-situ or in-situ relative to the CPBD chamber employed to characterize a sample. The process environment in which ETP may be performed may also vary based on the compositions and/or geometries of the two probe tips, among other possible factors. For example, ETP may be performed in an ambient environment (e.g., room temperature air) or an inert gas environment, possibly at an elevated temperature (e.g., about 1000° C.). ETP may alternatively be performed in a substantial vacuum, such as at a nominal or maximum vacuum attainable within a chamber of a CPBD.

Another probe preparation process that may be performed during the process 355 (and/or elsewhere in the method 300) is a cross-probe cleaning process. In one embodiment, a cross-probe cleaning process may include positioning the stem or body portions of two or more probes in close proximity, or in contact, in a mutually orthogonal orientation, such as forming a shape resembling a cross. However, in other embodiments the probes may not be mutually orthogonal, but may be oriented at a relative angle less than about 90 degrees (e.g., about 30 degrees). Thereafter, electrical current may be directed through the probes (possibly a single current if the probes are in physical contact), such that the probes are heated by resistive heating or otherwise to an elevated temperature. At high temperatures, oxides and/or other contaminants previously formed or deposited on the probe tips may dislodge. This process may be performed as an alternative to, or in addition to, one or more of the probe processing procedures described above.

The above-described APPS may include one or more of the foregoing probe preparation procedures, one or more of which may be implemented as a substantially automated process as described herein, although one or more of the probe preparation procedures may also or alternatively be partially automated and/or substantially manual. Nonetheless, in embodiments in which one or more probe preparation procedures are employed, and the one or more probe preparation procedures collectively terminate, the CR may communicate to the positioner control device or the CPBD that such collective termination has occurred, and/or that the probes are properly prepared for the subsequent, intended sample characterization. Such communication may also be implemented as a substantially automated function.

The method 300b may also include a process 380 by which probes and/or probe tips installed in a manipulator or other positioning device within a CPBD chamber can be exchanged with additional probes and/or probe tips stored within the CPBD chamber. For example, an end-effector rack located within the CPBD chamber and accessible by the manipulator may store replacement probes and/or probe tips which are substantially similar to those installed in a manipulator, such that one or more probes and/or probe tips that become excessively dull or contaminated can be replaced with sharper or cleaner probes and/or probe tips. However, the probes and/or probe tips stored in the end-effector rack may also be configured for a different type of measurement or detection of a sample characteristic relative to the type of measurement or detection for which the probes and/or probe tips installed in the manipulator are configured. Additionally, or alternatively, the probes and/or probe tips stored in the end-effector rack may be configured for measuring or detecting a different characteristic of the sample relative to the sample characteristic for which the probes and/or probe tips installed in the manipulator configured to measure or detect.

The exchange of probes and/or probe tips between the manipulator and the end-effector rack may be substantially manual, partially automated or substantially automated. In addition to the exchange of probes, probe tips and/or end-effectors, the process 380 may include processes for positioning the manipulator proximate the rack or other storage structure where the additional end-effectors are stored, testing exchanged end-effectors, and repositioning the manipulator towards a probe preparation area or the sample being examined, among other possible processes. One or more of the procedures of the process 380 may be implemented by instructions or sub-routines in the APS described above, such as in the CR associated with the APS.

The end-effector rack described may substantially resemble a rack structure, possibly similar to the apparatus 500 shown in FIG. 5 and described below. However, other end-effector storage structure configurations are also within the scope of the present disclosure. For example, the end-effector rack may be, include or resemble a revolving or static carousel, cartridge or other structure. The end-effector rack may also be or include electro-mechanical apparatus, such as may be employed to partially automate, substantially automated or otherwise assist dispensing end-effectors and/or replacing or rejuvenating end-effectors according to aspects of the present disclosure. However, for the sake of simplicity, reference herein to the end-effector rack The method 300b may also include a process 385 by which probes and/or probe tips can be rejuvenated by cleaning and/or shaping, for example. The rejuvenation of the process 385 may include one or more of the probe preparation processes described herein or otherwise within the scope of the present disclosure. The process 385 may be substantially manual, partially automated or substantially automated. For example, one or more of the procedures of the process 385 may be implemented by instructions or sub-routines in the APS described above, such as in the CR associated with the APS.

The method 300b may also include a process 340 by which a sample may be removed from a sample examination area within a CPBD, including completely removing the sample from the CPBD. Such removal may be substantially manual, partially automated or substantially automated. In one embodiment, after all desired characteristics of a sample have been measured or detected, the CR may execute instructions or sub-routines to return the manipulator or other positioner to the end-effector rack to exchange end-effectors, while simultaneously removing the examined sample and preparing a new sample for introduction into the CPBD chamber, which may be implemented by employing grippers, tweezers, and/or other tools and/or methods, including those known to those of ordinary skill in the art.

The method 300b may also include one or more procedures by which one or more samples internal or external to the CPBD chamber may be processed prior to and/or after examination. Such procedures may include ex-situ processing of two or more samples in parallel or in series, in-situ processing of two or more samples in parallel or in series, and/or ex-situ processing of one or more samples in parallel or in series with in-situ processing of one or more samples. Such processes may include a process 360 by which a device-under-test (DUT) may be de-processed, an ex-situ process 365 which may be employed to prepare a DUT for examination prior to introducing the DUT into the CPBD, and/or a process 370 by which a DUT may be transferred to or otherwise introduced into the CPBD, among other possible DUT processing procedures. Further examples include an in-situ process 375 by which a DUT which may be employed to prepare a DUT for examination once the DUT is introduced into the CPBD, a process 390 which may be employed to coarsely and/or precisely position or orient a DUT within the CPBD chamber, and a process 395 may be employed to remove a DUT from the CPBD, among other possible DUT processing procedures, as well as combinations of ones of these and other processes.

Thus, one or more embodiments of the method 300b may generally include a plurality of such DUT preparation procedures, which may collectively be referred to herein as DUT preparation 397. In the embodiment illustrated in FIG. 3B, the method 300b includes DUT preparation 397 which includes each of processes 360, 365, 370, 375, 390 and 395. Of course, in other embodiments, the method 300b may include DUT preparation 397 which varies from the embodiment shown in FIG. 3B.

A DUT may be substantially similar to one or more of the samples described above as capable of being examined within a CPBD to measure or detect characteristics thereof. Alternatively, a DUT may be or include at least a portion of a particular transistor or other device formed on or integral to such samples. Nonetheless, for the sake of simplicity, the terms "sample" and "DUT" may sometimes be interchangeable with regard to some aspects of the present disclosure.

The process 360 of method 300b may be or include one or more optional procedures for de-processing a sample. In one embodiment, such sample de-processing includes removing one or more layers of the sample to expose a feature of interest on the sample. The process 365 of method 300b may be or include one or more optional procedures for preparing a sample for introduction into the CPBD, including procedures other than the de-processing procedures of the process 360. One or both of the processes 360 and 365 may be substantially manual, partially automated or substantially automated. For example, such de-processing and/or sample preparation may be implemented by the CR as automatic processes of the APS. In one such embodiment, procedures for de-processing and/or preparing a sample are initiated, adjusted, and terminated by sensors operable to monitor the status of the procedure. The sensors and the CR communicate to effect the procedure as an automated process. While myriad procedures may be employed for sample preparation, examples include chemical cleaning (e.g., by HF dip), chemical-mechanical-polishing or chemical-mechanical-planarizing (collectively referred to herein as CMP), self-assembled monolayer (SAM) deposition (such as after cleaning to prevent oxidation), selective deposition of one or more conductive and/or passivation layers (e.g., to prevent oxidation), and selective deposition of liquid metal and/or non-oxidizing metal, among others.

The process 370 of method 300b may include transporting the sample into the CPBD chamber, possibly from a sample load station that may be substantially similar to or include a load lock, a wafer cassette, a wafer tape/ring, a GEL-PAK or other waffle pack, and/or a vacuum-release or other type of tray, among other means for securing a sample during transport. An automated sample transport system (ASTS) may be implemented as a part of the CR described above, for example, may be employed to load and unload samples relative to the CPBD chamber. For example, the ASTS may be implemented as a set of methods or sub-routines to monitor status and/or location of relevant devices, and/or to implement or provide commands.

The ASTS may be enabled by appropriate software and hardware to communicate information used by the CR and/or the RS. In addition to hardware and software supporting such communications, the ASTS may include or be associated with a transport mechanism configured to provide the physical, mechanical aspect of transferring samples between a sample load station and the sample chamber. For example, the transport mechanism may include one or more electric motors, piezoelectric motors, MEMS motors, and/or pneumatic actuators, among other motion imparting apparatus, and may also include apparatus or features employed for friction reduction.

The one or more in-situ procedures of the process 375 may include sample conditioning or other sample preparation that employs the CPBD, as well as focused-ion-beam (FIB) sputtering, non-liquid-metal-ion-source sputtering, ion gun sputtering, plasma cleaning, reactive gas cleaning and/or radical cleaning (e.g., to remove radicals), any of which can be implemented through instructions or sub-routines of the CR. In one embodiment, process 375 includes cleaning the sample in-situ with a method of plasma cleaning using an EVACTRON device commercially available from XEI Scientific, Redwood City, Calif. Generally, such devices can use a low-powered RF plasma to make oxygen radicals from air that then oxidize and chemically etch away hydrocarbons (e.g., from the interior surfaces of an SEM and/or samples, probes and other items therein). As described in operations manuals available with the EVACTRON device, the device is mounted on a specimen chamber port. The plasma itself is confined to the EVACTRON chamber, which prevents ion and electron bombardment damage to the instrument or sample. The radicals are carried out of the plasma into the whole of the specimen chamber by convection. These radicals oxidize hydrocarbons to make CO, $H_2O$, and $CO_2$ gases to be removed by a vacuum pump.

The process 380 may include grounding the sample at the point or location where it will be probed, possibly relative to the CPBD chamber. In one embodiment, the sample is grounded to the stage, platform or other structure supporting the sample within the chamber. However, the sample may be suspended within the chamber, such as by bonding, grasping or otherwise coupling one or more probes with one or more surfaces or features of the sample, wherein one or more additional probes may be employed acquire the desired sample characteristic.

In one embodiment of the method 300b, once a sample has been introduced into the CPBD chamber (e.g., by process 370) and optional in-situ sample preparation is performed (e.g., by process 375), the presence of the sample within the CPBD chamber may be communicated to the CR. Possibly upon also receiving information that probes are properly prepared and/or that the sample is adequately grounded within the CPBD chamber, the CR may access the RS and the positioner control device to locate the probe tips above contact point or other a feature of interest on the sample, among other actions. In this context, "above" the contact points refers to a position from which a final trajectory to the contact point can be determined and executed. For example, such a position from which the final trajectory originates may be normal to a plane in which the contact points collectively reside.

Figure 4:
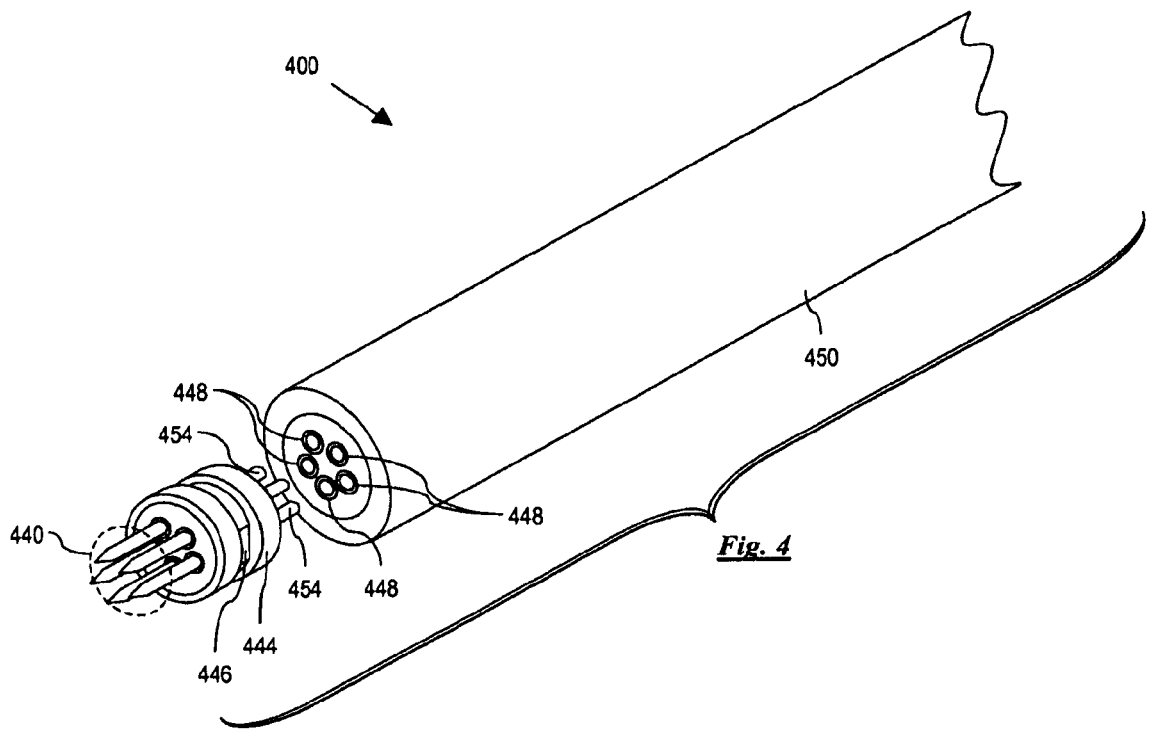
FIG. 4 is a perspective view of at least a portion of one embodiment of apparatus according to aspects of the present disclosure.

Referring to FIG. 4, illustrated is a perspective view of at least a portion of one embodiment of a positioner 400 according to aspects of the present disclosure. The positioner 400 is one example of the above-described positioners or manipulators that may each be employed to position one or more probes 440 employed during the measurement or detection of a characteristic of a sample being examined in a CPBD, such as within the apparatus 100 of FIG. 1 or the apparatus 200 of FIG. 2, and/or according to aspects of the methods 300a or 300b shown in FIGS. 3A and 3B, respectively. The positioner 400 and other manipulators within the scope of the present disclosure may have a resolution that is about equal to the resolution of the CPBD in which the positioner is employed, and/or about equal to the dimensions of the features being examined on a sample within the CPBD. In other embodiments, the resolution of the positioners may be greater (i.e., smaller increments) than the resolution of the CPBD and/or sample feature dimensions. Nonetheless, aspects of the present disclosure are also applicable to embodiments in which the positioner resolution is less than the resolution of the CPBD and/or sample feature dimensions.

For example, the probes 440 of the positioner 400 may be selected according to aspects of the selection process 305 of the method 300a shown in FIG. 3A. The probes 440 may also be exchanged according to aspects of the exchange process 380 of the method 300b, such as to replace dulled and/or contaminated probes with sharper and/or cleaner probes, or where probes of different utility are appropriate based on a particular characteristic being collected or a particular sample or sample feature being examined.

The positioner 400 may include an end-effector 444 to which the probes 440 may be permanently or detachably assembled. The probes 440 may be or include tungsten polycrystalline wire probes, possibly having a "stem" diameter ranging between about 0.25 mm and about 0.50 mm and a tapered tip, where the radius of curvature of the tip apex may be less than about 10 nm.

The end-effector 444 may be permanently or detachably coupled to a positioner body or handle 450. For example, a detachable coupling may be accomplished via one or more corresponding pairs of prongs 454 and sockets 448. Thus, in one embodiment, the end-effector 444 may include one or more examination probes (440) and one or more assembly probes (454, employable to assemble the end-effector 444 with the positioner 450). Each prong/socket pairing may correspond to one of the probes 440, as in the illustrated embodiment, or may correspond to more than one of the probes 440. Similarly, each socket 448 may be electrically connected to one or more leads extending from the body 450. However, other means for detachably coupling the end-effector 444 or probes 440 to the positioner 450 are also within the scope of the present disclosure.

The end-effector 444 may also be configured to be stored in or otherwise interface an end-effector rack, such as described above. In one embodiment, as illustrated in FIG. 4, the end-effector 444 may have one or more flats 446, and/or one or more other interfaces corresponding to or configured to cooperate with the end-effector rack. The flats 446 or another portion of the end-effector 444, including a portion configured to interface with an end-effector rack, may have a predetermined orientation relative to the probes 440, such that the orientation of the probes 440 may be known once the end-effector 444 is coupled to the body 450. For example, the flats 446 may include two substantially parallel flats on opposing sides of the end-effector 444, and the orientations of each of the probes 440 may be known relative to one or more edges or surfaces of the flats 446.

Figure 5:
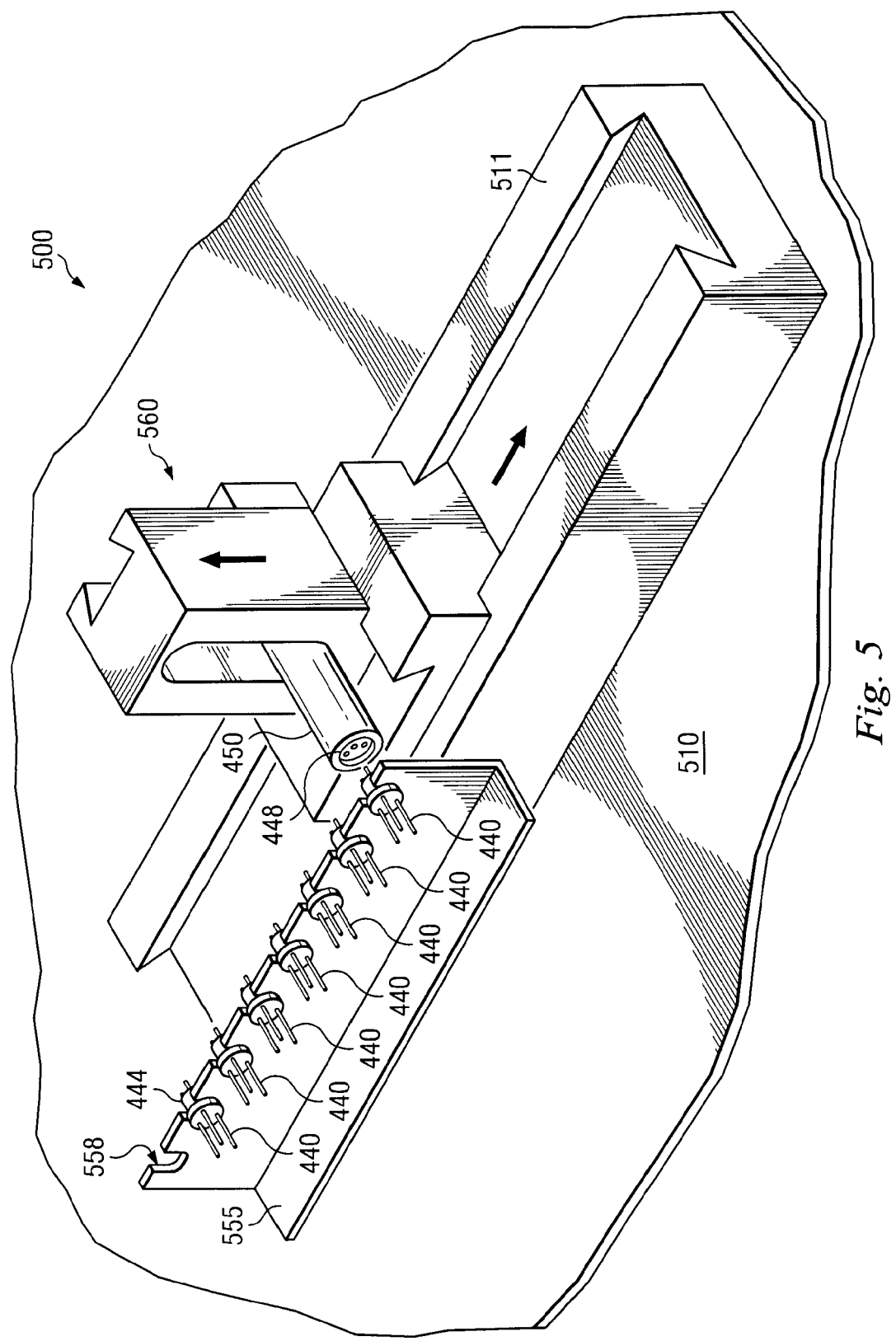
FIG. 5 is a perspective view of at least a portion of one embodiment of apparatus according to aspects of the present disclosure.

Referring to FIG. 5, illustrated is a perspective view of at least a portion of one embodiment of an apparatus 500 according to aspects of the present disclosure. The apparatus 500 includes an end-effector rack 555 which may be substantially similar to the end-effector rack(s) described above. The apparatus 500 also includes a plurality of end-effectors 440 which may be substantially similar to the end-effector 440 shown in FIG. 4. The apparatus 500 also includes a manipulator module 560 which may be substantially similar to the manipulator modules described above, such as the manipulator module 260 shown in FIG. 2. The manipulator module 560 may include a positioner or positioner body 450 which may be substantially similar to the positioner body 450 shown in FIG. 4.

The manipulator module 560 is coupled to a manipulator module interface 511 of a manipulation platform 510. The manipulator module interface 511 and the manipulation platform 510 may be substantially similar to the manipulator module interfaces 212 and the manipulation platform 210, respectively, shown in FIG. 2. For example, the manipulator module 560 and the manipulation platform 510 may be configured to be installed within a CPBD chamber, such as the CPBD 104 shown in FIG. 1 or the CPBD 104 shown in FIG. 2.

As shown in FIG. 5 and discussed above with regard to FIG. 4, a plurality of probes 440 may be assembled into respective end-effectors 444. However, in addition to probes 440, one or more tools, including those having different capabilities, may be assembled into one or more of the end-effectors 444. When an end-effector 444 so assembled is coupled with a positioner 450, the positioner 450 can have more than one measurement or detection capability, and possibly more than one manipulation capability. Such manipulation capability may used in conjunction with and/or in support of measurement and/or detection of one or more characteristics of one or more samples being examined within a CPBD. For example, multiple independent electrical probes 440 can be assembled in an end-effector 444, whereby a positioner 450 with such an end-effector 444 may be useful for measuring different kinds of samples. In addition, multiple positioners 450 equipped with end-effectors 444 having multiple probes 440 assembled therein can be used to take measurements according to the automated processes described herein.

In addition, features of any given sample may require that the probes 440 be reconfigured or moved independently. Thus, in some embodiments, one or more independent fine-motion positioners may be associated with one or more coarse-motion positioners, where one or more of the fine-motion and coarse-motion positions may be substantially similar to other positions or manipulators described herein, with the possible exception of scale.

The probes 440 assembled in an end-effector 444 coupled with a positioner 430 may be reconfigured to enable measurements of samples having different feature configurations. For example, some of the probes 440 may be flexible, such that they can be reconfigured with micro-scale and/or nano-scale embodiments of the positioners described herein or otherwise. In one embodiment, a first positioner may be oriented proximate a second positioner such that the first positioner may grasp or otherwise interface the second positioner or one or more probes assembled in the second positioner, such as to pull, bend or otherwise reposition the one or more probes after their initial orientation by the second positioner. These and other manipulations within the scope of the present disclosure may be performed before or after the probes are introduced into the sample chamber of a CPBD (i.e., either ex-situ or in-situ relative to the CPBD).

In one embodiment, the probes 440 are assembled into the end-effectors 444, and the end-effectors 444 are arranged in the end-effector rack 555, such as in one or more of the illustrated end-effector stations 558 configured to receive and retain an end-effector 444 when not being used to measure or detect sample characteristics. The end-effectors 444 may be installed in the end-effector rack 555 by an ex-situ or in-situ process, which may be substantially manual, partially automated or substantially automated. Thereafter, the end-effector rack 555 may be coupled to a manipulator module interface 511 of the manipulation platform 510, either before or after the manipulation platform 510 has been positioned within a CPBD chamber.

The end-effector rack 555 may be introduced into the CPBD chamber by one or more processes which may collectively be substantially manual, partially automated or substantially automated. For example, prior to introduction into the CPBD chamber, the end-effector rack 555 may be introduced into a load lock where sensors may determine pressure and/or other conditions of the load lock and/or CPBD chamber, and such conditions may be communicated to the above-described CR to determine when the proper conditions exist for transporting the end-effector rack 555 from the load lock into the CPBD chamber. One embodiment of a substantially automated process by which the end-effector rack 555 may be transported from the load lock to the CPBD chamber includes the use of a feeder, a conveyor, a parts loader, or similar transfer mechanisms, including those that may be equipped with location sensors or other location features. The transfer mechanism may also be configured to communicate to the CR information regarding when an end-effector 444 has been positioned within the CPBD chamber.

Once the end-effector rack 555 has been positioned within the CPBD chamber, exchange of an end-effector 444 from the end-effector rack 555 to a positioner 450 may be accomplished, such as by presenting the rack 555 to the positioner 450. A positioning stage of the manipulator module 560 may position the rack 555 and the positioner 450 so that prongs 454 of an end-effector 444 and sockets 448 of a positioner 450 are coincident. The positioning stage may then translate or otherwise move away from the end-effector station 558, such as in a direction consistent with the function of the illustrated "U" shaped geometry of the end-effector station 558. Of course, one or more of the end-effector stations 558 may have other geometries. This process may also be reversed, substantially, such as may be employed to exchange an end-effector 444, or other processes in which an end-effector 444 may be returned or otherwise assembled to the end-effector rack 555 by using a positioner 450. Such processes may by substantially manual, partially automated or substantially automated, possibly in a similar manner as the removal of an end-effector 444 from the end-effector rack 555. For example, communications may be determined and sent by and through operations of a positioner control device or other feature configured to control operation of the positioner 450, and communications may also be determined and sent by and through operations of the CPBD and/or the CR.

Figure 6:
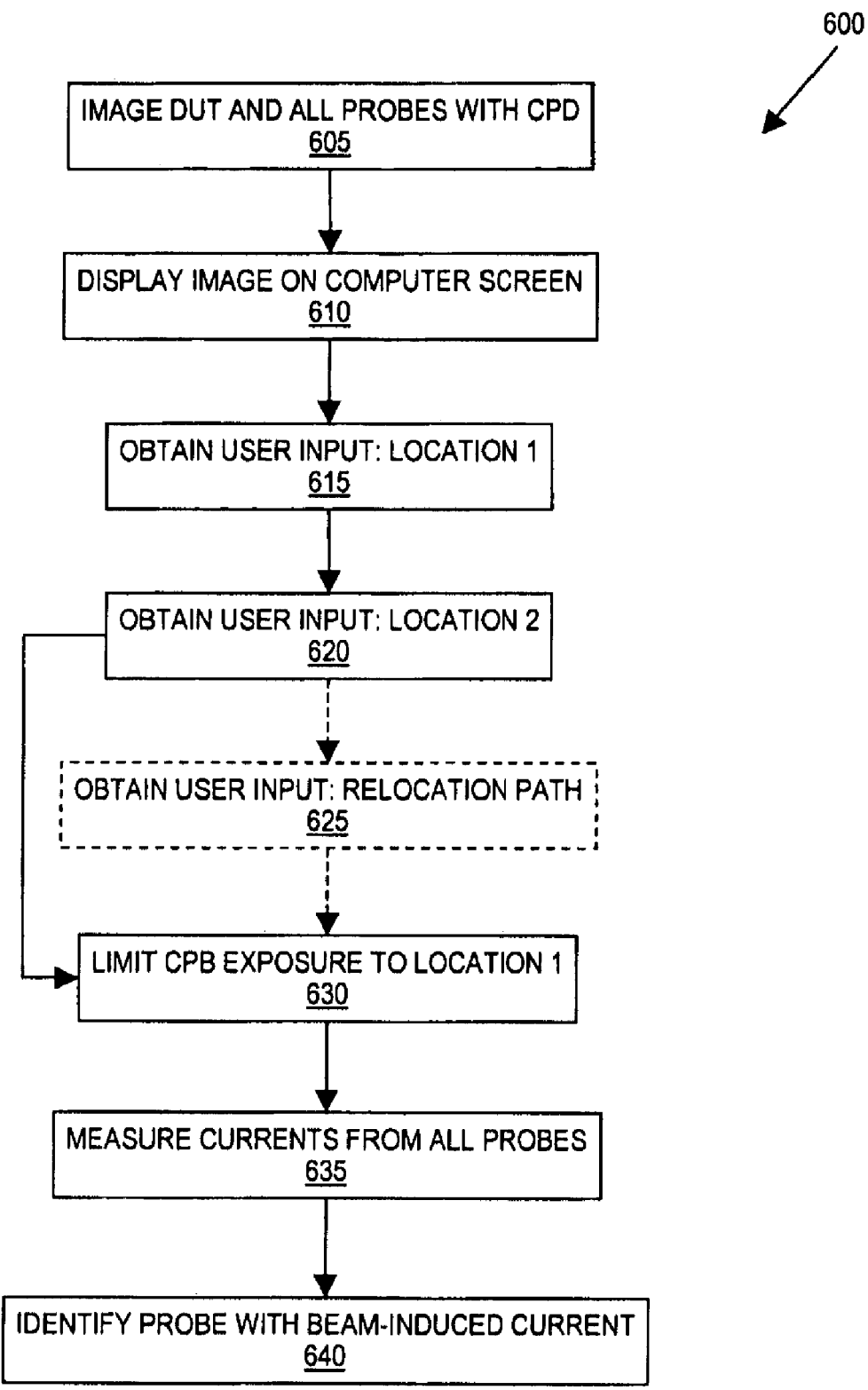
FIG. 6 is a flow-chart diagram of at least a portion of one embodiment of a method according to aspects of the present disclosure.

Referring to FIG. 6, illustrated is a flow-chart diagram of at least a portion of one embodiment of a method 600 according to aspects of the present disclosure. The method 600 may be employed in a partially or substantially automated point-and-click process, and/or in or with the above-described RS, such as for probe positioning. Thus, for example, the method 600 may be implemented in or performed by the apparatus 100 of FIG. 1 or the apparatus 200 of FIG. 2. Consequently, the method 600 may be performed in conjunction with the apparatus 400 shown in FIG. 4 and/or the apparatus 500 of FIG. 5. The method 600 may also be used or performed in conjunction with embodiments of the methods 300a or 300b shown in FIGS. 3A and 3B, whether in a substantially parallel, serial or interlaced manner. The method 600 may also be implemented in accord with the APS, CR and/or RS described above.

The method 600 may be performed to achieve probe positioning that is guided by probe-current imaging. Aspects of probe-current imaging may be similar to aspects of specimen-current imaging, a process known by those skilled in the art. However, according to aspects of probe-current imaging, electrical current is conducted through the probe in contrast to (or in addition to) electrical current conducted through a sample under investigation. Probe-current imaging may include measuring current from or between one or more probes, a sample and/or ground, such as a functions of the raster location or coordinates of the CPB of a CPBD (as a "map," for example).

When a semi-automated point-and-click process is used, the probing process may at least temporarily depart from any then-functioning automation scheme. However, once probes have been properly located above contact points, such automation may resume, such as where a positioner control device may communicate signals to CR, which may loop the probing back into the automated scheme.

The method 600 includes a process 605 by which a DUT (device-under-test) may be imaged, such as by an SEM or other CPBD. The process 605 may also include imaging one or more probes with the CPBD, possibly including all of the probes that may be assembled to a positioner or otherwise controlled by a manipulator module or positioned control device. The DUT and the imaged probes are then displayed on a computer screen or other display device associated with the CPBD in a process 610.

User input may then be received by a process 615. For example, a user viewing the display of the process 610 may indicate which of the imaged probes is desired to be located from its imaged location. Such indication may be in the form of a mouse click, where the user manipulates a mouse to locate a pointer over the image of the desired probe or other imaged feature and then clicks a button on the mouse. Of course, user input means other than or in addition to computer mouse operations are also within the scope of the present disclosure. For the sake of simplicity, the initial, imaged location of the probe selected by the user will be referred to as Location 1.

A subsequent process 620 also includes receiving user input. However, during this process, the user indicates a location to which the user desires the probe selected during the process 615 is to be translated. For the sake of simplicity, this target location indicated by the user may be referred to as Location 2. The user may indicate Location 2 in a manner substantially similar to the user's indication of Location 1 (e.g., by mouse-click).

The target location may be substantially coincident with the contact point or other feature of interest on a sample being examined. However, the target location and feature of interest may not be substantially coincident in some embodiments within the scope of the present disclosure. For example, some devices being examined within the CPBD may be damaged by direct exposure to the CPB of the CPBD. In such scenarios, and possibly others, the target location may merely be in the vicinity of the feature of interest, but not coincident, such as when the target location may be slightly offset from the feature of interest, possibly in a direction conforming to a probe relocation path.

The method 600 may also include a process 625 facilitating the receipt of user input indicating a desired or preferred relocation path. For example, a user may desire that the relocation path along which the selected probe should travel to the target location (i.e., the path connecting Location 1 and Location 2) may avoid an obstacle or area of the DUT or sample, or that this relocation path be the shortest path possible. In another example, the user may desire that the relocation path comprise a plurality of arcs connected end-to-end, possibly having substantially similar radii, or a plurality of similarly-shaped loops.

The method 600 proceeds from one of process 620 and the process 625 to a process 630 during which the SEM or other CPBD device may be adjusted to limit exposure of its charged particle beam (CPB) to the probe selected by the user during the process 615. For example, the CPBD may be switched to a spot mode (in contrast to a raster mode, an unfocused mode, or a broader illumination mode, for example), and the subsequently narrowed CPB may be focused on the selected probe. In another embodiment, the non-selected probes may be hidden, sheltered or masked from the CPB, or other processes may be performed such that only the probe selected during the process 615 may be exposed to the CPB. The exposure of the selected probe to the CPB may continue during subsequent processes or steps of the method 600.

Electrical current (e.g., to ground or an electrical reference point of the CPBD) is measured in each of the probes during a process 635. In one embodiment, current may only be measured in a limited number of the plurality of probes within the CPBD chamber, although this sub-set of probes includes the probe selected by the user during the process 615.

The probe currents may be measured in a conventional manner. Those skilled in the art are familiar with the myriad, commercially available apparatus which may be employed for such probe current measurement, such as electrometers and various amplifiers, among others. Nonetheless, other apparatus are also within the scope of the present disclosure.

The method 600 also includes a process 640 by which the probe that is exposed to the CPB by the process 630 is identified. For example, the current measured from the probe exposed to the CPBD may be greater in magnitude than the current measured from the other probes.

Figure 7:
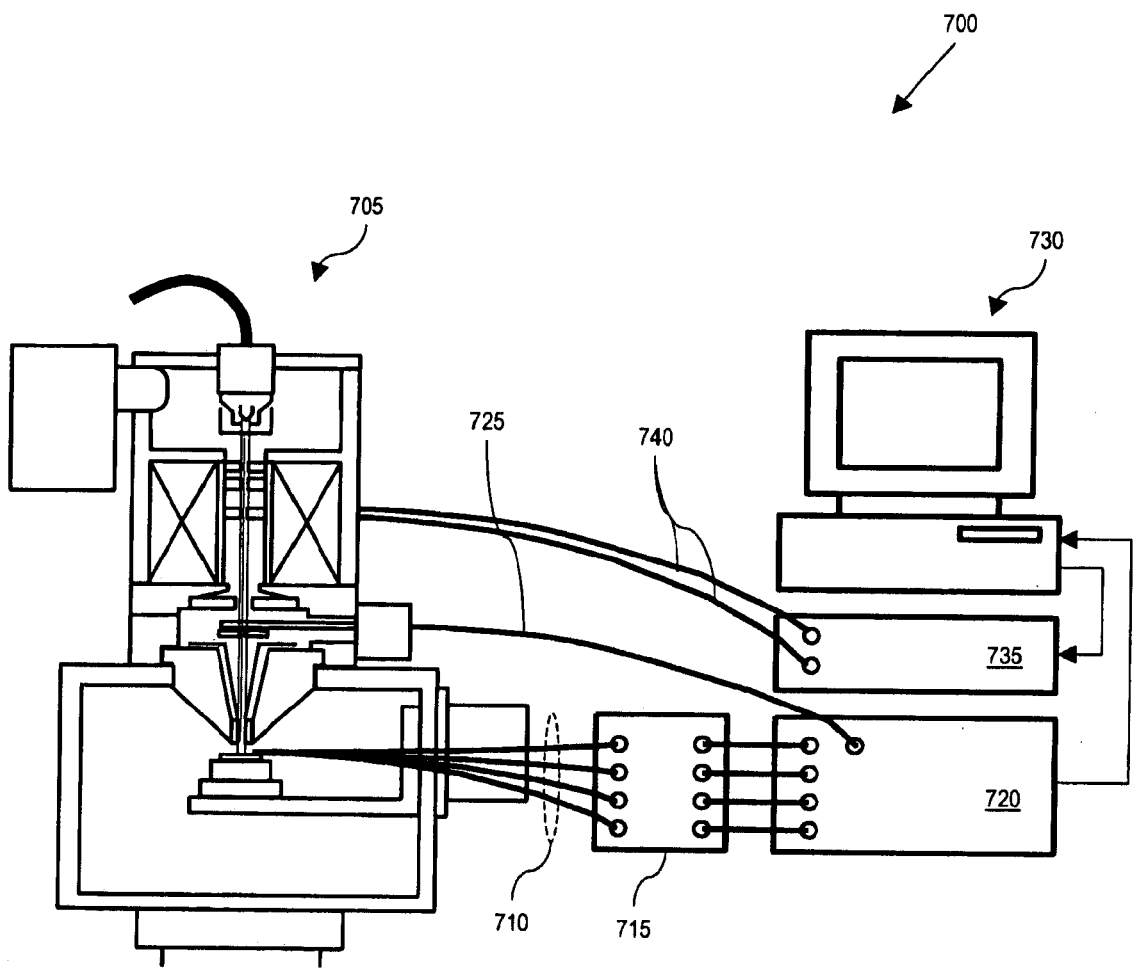
FIG. 7 is a block-diagram of at least a portion of one embodiment of apparatus according to aspects of the present disclosure.

Referring to FIG. 7, illustrated is a block diagram of at least a portion of one embodiment of an apparatus 700 according to aspects of the present disclosure. The apparatus 700 is one example of apparatus that may be employed to perform the method 600 shown in FIG. 6, or may otherwise may be employed during performance of the method 600.

The apparatus 700 includes or is coupled to or otherwise associated with an SEM or other CPBD 705 having a chamber in which one or more probes may be utilized according to aspects of the present disclosure. The current in each probe is communicated via cables 710 to a current-to-voltage converter 715. Voltage signals corresponding to each of the probes may thus be communicated to an analog-to-digital converter (ADC) 720 or another device having such conversion capabilities, which may also be configured to communicate video signals with the CPBD 705 via cabling 725.

The ADC 720 may be in communication with a computer (e.g., a personal computer) 730 and a digital-to-analog converter (DAC) 735. One or both of the ADC 720 and the DAC 735 may be integral components or functions of the computer 730, although they may also be discrete components coupled to the computer 730. The DAC 735 may also be in communication with the CPBD 705, such as through cabling 740. Such communication may regard the control of one or more aspects of the CPBD 705, such as the deflection or other aspects of the CPB.

In one embodiment of operation of the apparatus 700, such as in accord with the method 600 of FIG. 6, an imaging unit the CPBD 705 may be employed to generate an image of a DUT and one or more probes oriented within the chamber of the CPBD 705, such that an image of the DUT and probes may be displayed on a screen of the computer 730. Thereafter, a user may select one of the probes displayed in such image, such as by using a mouse to position a pointer on the display screen over the image of the desired probe and pressing a button on the mouse. The user may also reposition the pointer to another site on the DUT displayed in the image on the screen of the computer 730 and again press a mouse button to indicate a target location to which the selected probe is to be positioned.

Thereafter, the CPBD 705 may automatically switch to a "spot" mode, such as in response to receiving the user input regarding the target location, or the CPBD 705 may be manually switched to "spot" mode by the user. The narrowed CPB generated in the CPBD 705 may then be directed to the previously selected probe, or to the location corresponding to the location of the previously selected probe, as indicated by an increased current measured from the selected probe by the converter 715 and/or the ADC 720, among other possible components.

Figure 8:
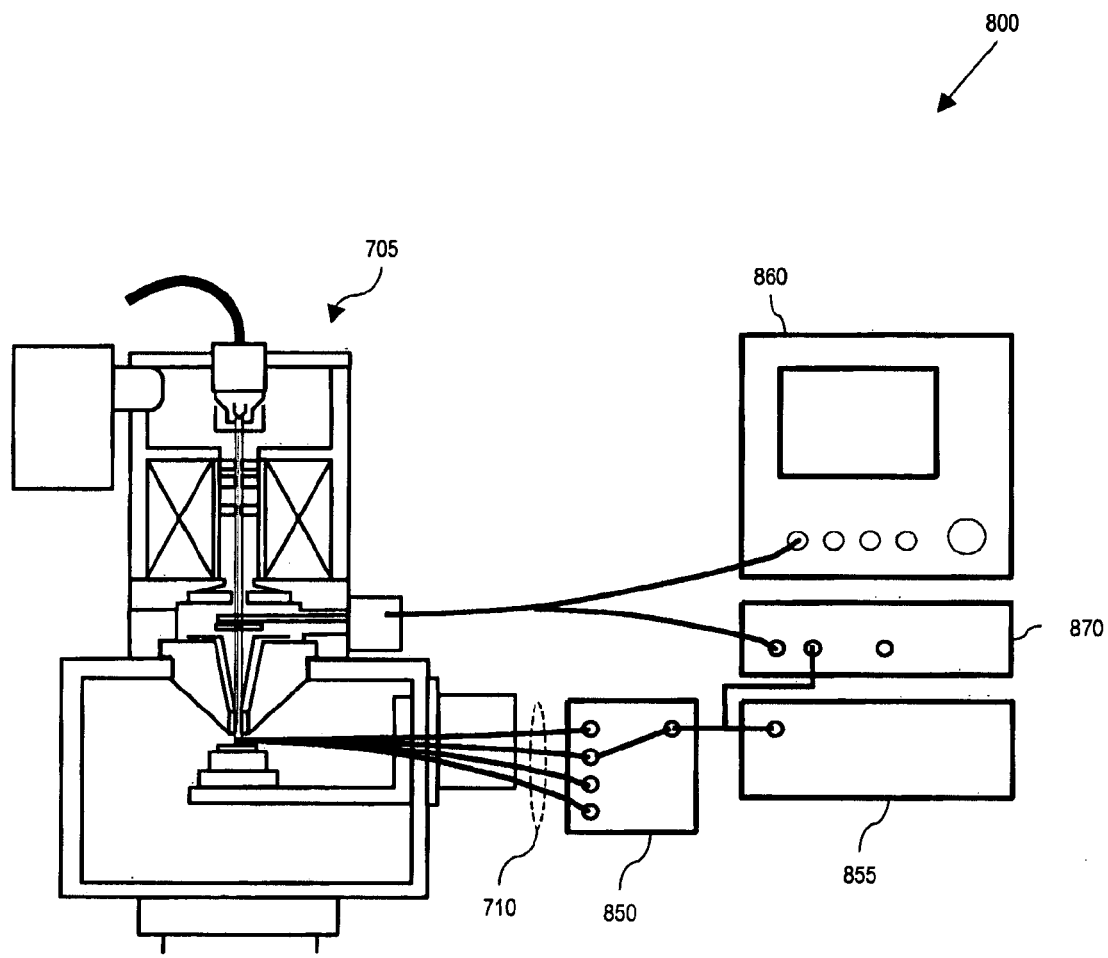
FIG. 8 is a block-diagram of at least a portion of one embodiment of apparatus according to aspects of the present disclosure.

Referring to FIG. 8, illustrated is another embodiment of the apparatus 700 shown in FIG. 7, herein designated by the reference numeral 800. The apparatus 800 may include or be associated with a CPBD 705 that may be substantially similar to the CPBD 705 shown in FIG. 7. However, the cabling 710 extending from probes located within the chamber of the CPBD 705 extend to a selector 850, whereby a reference signal may be communicated from a signal generator 855 to a selected one of the probes.

The reference signal may also be communicated from the signal generator 855 to a console or other device 860 having display functionality and associated with the CPBD 705. A video signal from the CPBD 705 may also be communicated to the console 860. A comparison of the video signal from the CPBD 705 and the reference signal from the generator 855 may also be employed to determine which probe is exposed to the CPB generated by the CPBD 705 or which probe is being driven by the signal from the generator 855. For example, a manual, partially automated or substantially automated comparison may reveal a similarity between the video signal generated from the CPBD 705 and the reference signal being communicated to one of the probes.

In one embodiment, the apparatus 800 may be used to perform the method 600 of FIG. 6, wherein the probe-current detection/imaging may be replaced by the comparison of the reference signal and the video signal. For example, a comparator unit 870 may be employed for such comparison.

Figure 9:
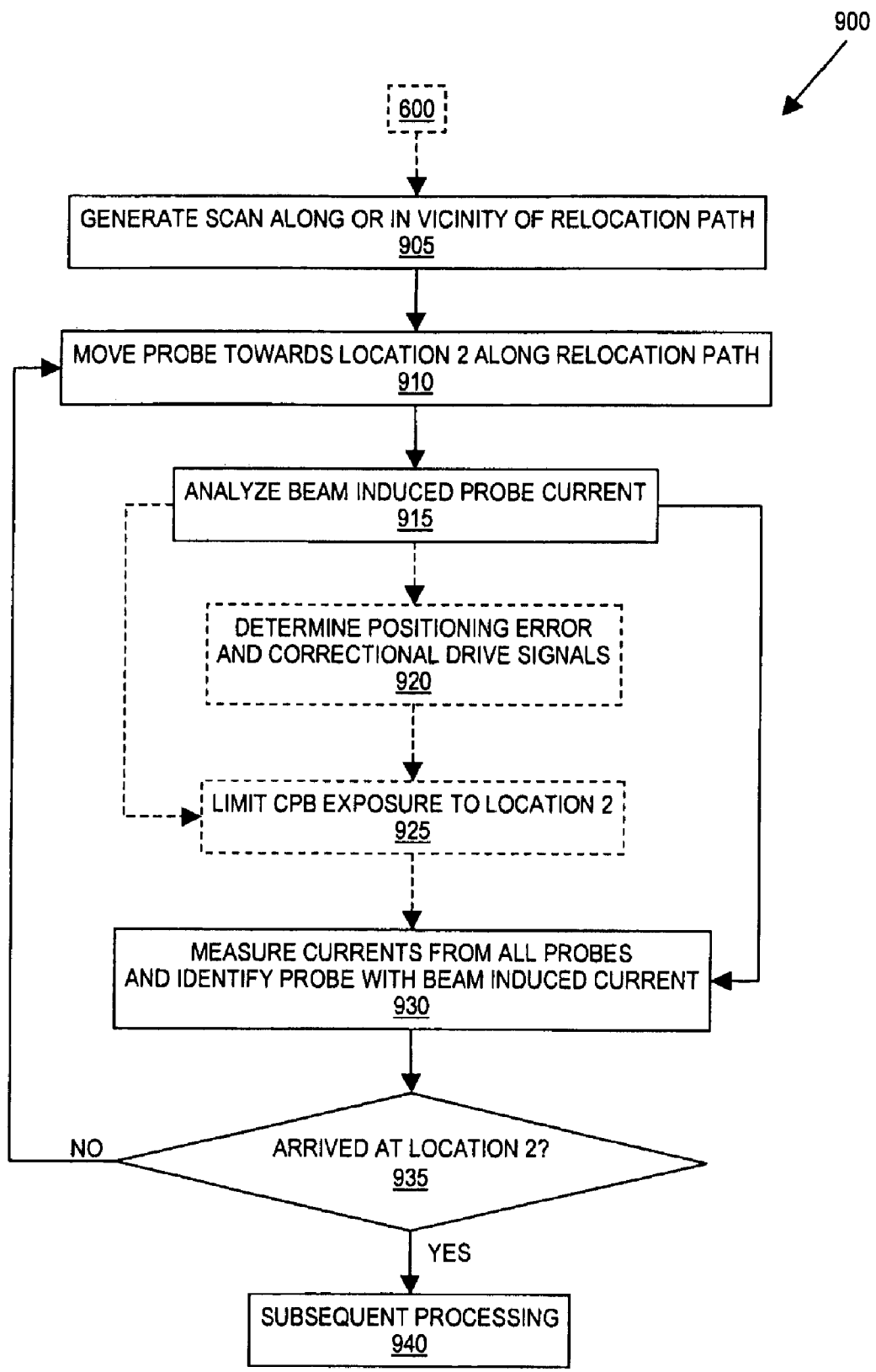
FIG. 9 is a flow-chart diagram of at least a portion of one embodiment of a method according to aspects of the present disclosure.

Referring to FIG. 9, illustrated is a flow-chart diagram of at least a portion of one embodiment of a method 900 according to aspects of the present disclosure. The method 900 may be employed in a partially or substantially automated process for probe positioning. Thus, for example, the method 900 may be implemented in or performed by one or more of the apparatus 100 of FIG. 1, the apparatus 200 of FIG. 2, the apparatus 700 of FIG. 7 and the apparatus 800 of FIG. 8. Consequently, the method 900 may be performed in conjunction with the apparatus 400 shown in FIG. 4 and/or the apparatus 500 of FIG. 5. The method 900 may also be implemented in accord with the APS, CR and/or RS described above.

The method 900 may also be used or performed in conjunction with embodiments of the methods 300a or 300b shown in FIGS. 3A and 3B and/or the method 600 shown in FIG. 6, whether in a substantially parallel, serial or interlaced manner. For example, as in the illustrated embodiment, the method 900 may substantially include the method 600 of FIG. 6. Consequently, the method 900 may include one or more processes for determining and/or receiving current and target locations for a selected probe (possibly referred to herein as Location 1 and Location 2, respectively), as well as a user-desired relocation path connecting the current and target locations.

The method 900 may be performed to achieve probe positioning that is guided by probe-current imaging. When a semi-automated process is used, such as a point-and-click process, the probing process may at least temporarily depart from any then-functioning automation scheme. However, once probes have been properly located above contact points, for example, such automation may resume, such as where a positioner control device may communicate signals to CR, which may loop the probing back into the automated scheme.

The method 900 may also include a process 905 by which a scan or probe trajectory may be generated. The scan may be substantially similar or identical to a relocation path that may be received as user input, such as during the process 625 of the method 600. In other embodiments, the scan generated by the process 905 may merely approximate such user-input relocation path, possibly falling within the substantial vicinity of the user's relocation path. However, in one embodiment, the scan generated during the process 905 may have little similarity to the user's relocation path, other then its endpoints (e.g., initial and target locations, or Location 1 and Location 2 referred to above with regard to FIG. 6).

During a process 910 of the method 900, the selected probe may be translated towards the target location, whether along the relocation path or otherwise. Such translation may be substantially limited to lateral movements, such as those being substantially parallel to the surface of the DUT or sample, or may also include a directional component that is substantially perpendicular to the surface of the DUT. The translation of the probe during the process 910 may also not be limited to translation, but may also include rotational movement about one or more axes of rotation. Thus, translation of one or more probes within the scope of the present disclosure may, at times, refer to both translation and rotation, which may collectively be referred to as positioning, repositioning, orientation and/or reorientation.

The current in the translated probe, including current induced by the CPB generated by the CPBD, may be measured in a process 915 of the method 900. The current measurement of the process 915 may be a single measurement, or multiple periodic or randomly intermittent measurements, or even substantially continuous measurement. The process 915 may also include measuring current in probes other than or in addition to the probe being repositioned. Such current measurement may be performed by one or more functions or components of the apparatus 700 of FIG. 7 and/or the apparatus 800 of FIG. 8. In one embodiment, such aspects may be employed in or for collision avoidance processes and protocols, such as to prevent collisions between probes and other objects within the chamber of the CPBD.

The method 900 may also include a process 920 during which positioning error may be determined for the probe being repositioned. For example, the probe-locating processes described herein may be employed to determine any difference between a desired location and the actual location of the probe. The process 920 may also include generating correctional drive signals which may be employed to correct any detected positioning error. The error and/or correction processes of the process 920 may be performed once, repeatedly at periodic or random intervals, or substantially continuously.

The method 900 may also include a process 925 by which exposure of the CPB generated by the CPBD may be limited to the target location. The process 925 may be substantially similar to the process 630 shown in FIG. 6.

A process 930 of the method 900 may include measuring current from a plurality of the probes in the CPBD, including the probe being repositioned, and identifying any probe having a greater current induced by the CPB. The process 930 may be substantially similar to the combination of the processes 635 and 640 of FIG. 6.

The information gathered during the process 930, among other processes of the method 900, can be used to determine whether the probe being repositioned has arrived at its target location. For example, if the exposure of the CPB is limited to the target location by the process 925 described above, then the detection of an increased current induced in the probe being repositioned to the target location may provide an indication that the probe has successfully been repositioned in its target location. A decisional step 935 may be included in the method 900 to query whether the selected probe is arrived at its target location. The method 900 may thus proceed to processes for repositioning additional probes or otherwise end operations directed towards positioning the selected probe, collectively indicated in FIG. 9 by the "SUBSEQUENT PROCESSING" process 940, if it is determined during the decisional step 935 that the selected probe has successfully reached its target location. Alternatively, if the selected probe requires additional positioning, a portion of the method 900 may be repeated for the selected probe, possibly starting with the process 910, as shown in FIG. 9.

Figure 10:
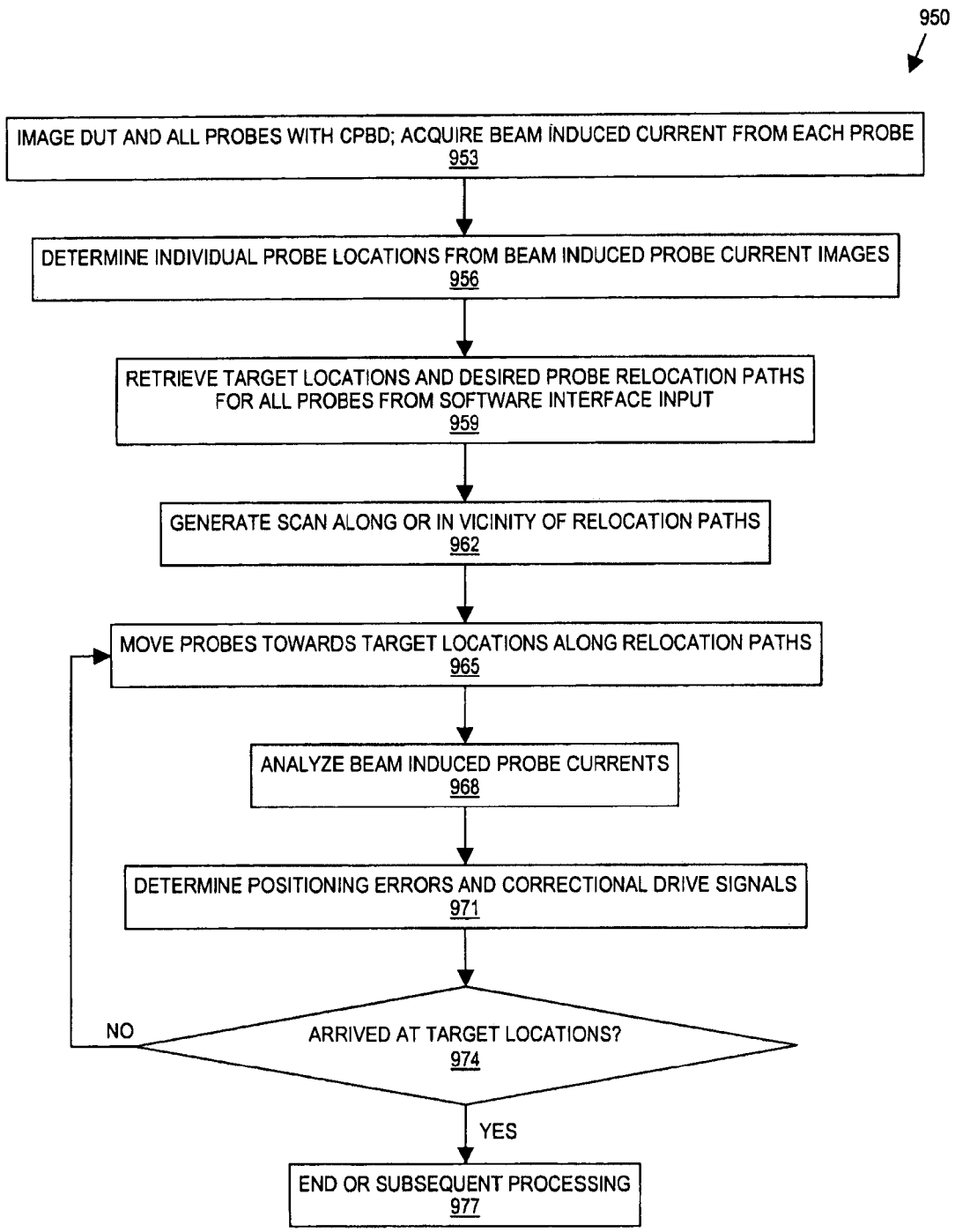
FIG. 10 is a flow-chart diagram of at least a portion of one embodiment of a method according to aspects of the present disclosure.

Referring to FIG. 10, illustrated is a flow-chart diagram of at least a portion of one embodiment of a method 950 according to aspects of the present disclosure. The method 950 may be employed in a partially or substantially automated point-and-click process for probe positioning. Thus, for example, the method 950 may be implemented in or performed by one or more of the apparatus 100 of FIG. 1, the apparatus 200 of FIG. 2, the apparatus 700 of FIG. 7 and the apparatus 800 of FIG. 8. Consequently, the method 950 may be performed in conjunction with the apparatus 400 shown in FIG. 4 and/or the apparatus 500 of FIG. 5. The method 950 may also be implemented in accord with the APS, CR and/or RS described above. The method 950 may also be used or performed in conjunction with embodiments of the methods 300a or 300b shown in FIGS. 3A and 3B, the method 600 shown in FIG. 6, and/or the method 900 of FIG. 9, whether in a substantially parallel, serial or interlaced manner. Several aspects of the individual processes of the method 950 may be substantially similar to corresponding processes of the method 900 of FIG. 9, in which case the descriptions of the processes in the method 900 may also apply to one or more processes in the method 950.

The method 950 may be performed to achieve probe positioning that is guided by probe-current imaging. When a semi-automated point-and-click process is used, the probing process may at least temporarily depart from any then-functioning automation scheme. However, in one embodiment, the method 950 may allow the probing process to substantially remain within any such automation scheme. For example, when the positioning procedure for a selected probe determines that the probe has reached the desired location (e.g., with respect to contact points on the DUT or sample being examined), the CR or other function or apparatus may signal the positioner control device or other device controlling probe positioning, which may initiate procedures for bringing the probe tips into physical and electrical contact with the desired contact points. This process may be referred to herein as "touch-down" of the probe tips, and may be substantially similar to the process 320 of FIGS. 3A and 3B.

During touch-down, a positioner control device may translate the probes down and into physical and electrical contact with contact points on the sample. When more than one probe is being used, the probes may be lowered simultaneously, in groups, or one at a time, depending on the programming of the positioner control device. In one embodiment, the CR includes a procedure to cause the positioner control device to keep the probes in the proper position after successful touch-down and until the measurement is completed. As a tip makes contact, it may send a signal back to the positioner control device, which may activate a sub-routine of the CR. The activated sub-routine may provide an automated process for determining the quality of the contact made with the sample.

The method 950 includes a process 953 during which a DUT and associated probes are imaged with a CPBD, and any current in the probes is acquired, including any current induced by the CPB generated by the CPBD. Aspects of the process 953 may be substantially similar to those described above.

In a subsequent process 956 of the method 950, individual locations of each of the probes is determined, such as from an image of the beam-induced currents or of all probe currents. The method 950 may also include a process 959 during which target locations may be received, such as from user input, possibly in conjunction with corresponding relocation paths. However, the information may also be retrieved and/or input from a software interface, such as software that may be employed with a map of the DUT.

The method 950 may proceed to a process 962 during which scans are generated along or in the vicinity of the relocation paths determined in the process 959, such that one or more probes may be translated along one or more corresponding relocation paths during a process 965. Current may then be measured in each translated probe and subsequently analyzed during a process 968, including any beam-induced currents. Such currents may be employed during a process 971 to determine any positional errors and/or generate correctional drive signals. One or more of the processes 965, 968 and 971 may be repeated until, as possibly determined by a decisional step 974, each of the probes being translated successfully arrives at its corresponding target location, at which time the method 950 ends or proceeds to additional processes.

Figure 11:
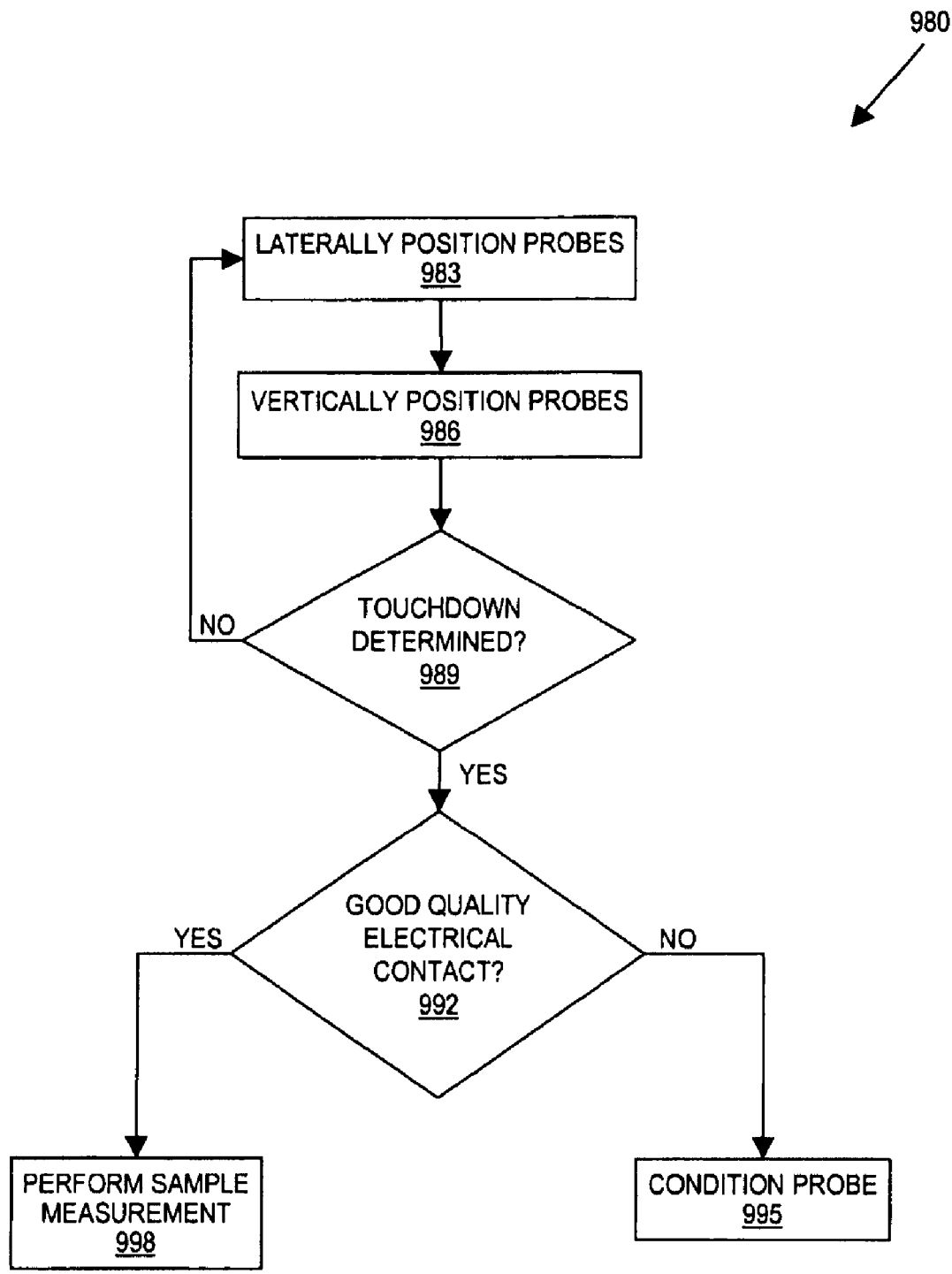
FIG. 11 is a flow-chart diagram of at least a portion of one embodiment of a method according to aspects of the present disclosure.

Referring to FIG. 11, illustrated is a flow-chart diagram of at least a portion of one embodiment of a method 980 according to aspects of the present disclosure. The method 980 may be employed in a substantially manual, a partially automated or a substantially automated point-and-click process for probe positioning. Thus, for example, the method 980 may be implemented in or performed by one or more of the apparatus 100 of FIG. 1, the apparatus 200 of FIG. 2, the apparatus 700 of FIG. 7 and the apparatus 800 of FIG. 8. Consequently, the method 980 may be performed in conjunction with the apparatus 400 shown in FIG. 4 and/or the apparatus 500 of FIG. 5. The method 950 may also be implemented in accord with the APS, CR and/or RS described above. The method 950 may also be used or performed in conjunction with embodiments of the methods 300a or 300b shown in FIGS. 3A and 3B, the method 600 shown in FIG. 6, the method 900 of FIG. 9, and/or the method 950 of FIG. 10, whether in a substantially parallel, serial or interlaced manner.

The method 980 may be employed to determine physical and electrical contact with contact points on a DUT or sample within the chamber of a CPBD. For example, a process 983 may initially be performed to position one or more probe over a contact point, where such positioning may primarily be in a plane that is substantially parallel to a surface of the sample. Thereafter, a process 986 may vertically position the probes, such as in a direction that is substantially perpendicular to the sample surface. The method 980 includes a decisional step 989 by which the positioning processes 983 and 986 may be repeated if "touch-down" is not determined.

However, if no additional positioning is determined necessary during the decisional step 989, an additional decisional step 992 of the method 980 may assess the adequacy of the electrical contact between the probes and their corresponding contact points on the sample. For example, if the electrical contact between a probe and a contact point is such that electrical resistance between the probe and contact point is excessive, the probe may be conditioned, characterized, cleaned or otherwise processed during a process 995, such as according to one or more of the probe preparation procedures described above. However, if the electrical contact between a probe and contact point is satisfactory (e.g., good ohmic contact), the intended measurement or detection of a characteristic of the sample may be performed, as indicated by the process 998 of the method 980.

Thus, contacting a probe and a sample contact point may include laterally positioning of the probe over the sample contact point, vertically positioning the probe until physical contact is made between the probe and the contact point, verifying the physical contact via the touch-down processing described above, and verifying the electrical quality of the contact between the probe and contact point. Moreover, the method 980 may be substantially manual, partially automated or substantially automated according to aspects of the present disclosure. For example, the process 989 may include executing a sub-routine of the CR to determine whether physical contact between the probe and sample exists. The sub-routine may comprise programming to instruct a positioner control device or the CPBD to implement a procedure that obtains information indicative of physical contact between the probe tip and the sample. Such procedures may include: (1) detecting capacitance (AC and/or DC); (2) detecting force; (3) enabling visual observations of the probe tip and the sample; (4) scanning probe imaging methods; (5) observations of a mechanical pivot (vision); (6) determination of interaction with the CPB; and/or (7) using EDX for positioning information energy dispersive x-ray analysis.

One embodiment of a capacitance-based procedure for determining probe-sample contact involves determining the capacity or change in capacity between the probe and the sample. An embodiment of a force-detection procedure for determining probe-sample contact may employ a force sensor that signals when localized forces meet or exceed a threshold value, which may indicate close proximity or mechanical contact of the tip with the contact point of the sample. Force-detection procedures can also be implemented with cantilevers or other springs combined with position detectors, whereby a spring constant may be used to calculate probe deflection as a function of force. Scanning probe imaging methods for determining probe-sample contact may provide data by which a signal indicating contact can be generated.

With regard to mechanical pivot observation methods for determining probe-sample contact, mechanical contact of the probe can create a pivot point. Detection of any pivoting or rotation of the probe around a pivot point may be indicated by lateral deflections of the probe which may be analyzed with simultaneously acquired images of the CPB to reveal indications of mechanical contact of the probe. The existence of the pivot point, and optionally the location of the pivot point, may be communicated by the CPBD as a signal that touch-down has been made. With regard to EDX-based determination of probe-sample contact, x-rays induced by the CPB may interact with the sample and subsequently be analyzed to obtain information regarding the elemental composition of the sample, thereby supporting identification of the site to be contacted.

These and other aspects of the method 980 may be implemented as an automated process within the APS, or as a semi-automated process performed outside of the APS subsequently reintroduced into the APS upon communications confirming that physical contact has been made. Consequently, the CR may initiate an additional sub-routine or set of procedures for determining that electrical contact has been made between the probe tip and the contact point. Alternatively, prior to determining electrical contact, sub-routines can be implemented by the CR to cause certain procedures to be performed to improve the probability that the probe tips have not only physically contacted the contact points, but have also electrically contacted the contact points, and remain in good electrical contact with the contact points.

In one embodiment, such as according to certain procedures suitable for improving the probability of electrical contact, communications are sent between the CR and the positioner control device employed to position the probes. Suitable procedures may include: (1) scrubbing, which comprises moving the probe around, and "digging" into the contact; (2) using a separate "chisel probe," which comprises employing another tip in to roughen up the contact surface; and (3) using a hammer probe, which comprises employing a probe to "hammer" another probe into the contact surface. Each such procedure can be implemented as a partially or substantially automated process by appropriate programming within the CR and communications between the CR and the positioner control device.

Some processes for improving the probability of adequate electrical contact between a probe and sample contact point may be implemented in an ex-situ or in-situ probe preparation or sample preparation process. One such method includes dipping or coating the probe and/or sample with a metal that melts at a temperatures low enough to not damage the probe or sample. Consequently, the metal may "wet" the sample contact point, possibly increasing the likelihood of satisfactory ohmic contact because one or both of the probe and the sample contact point is allowed to contact softer metal. In one such embodiment, the metal may be one that will alloy with the probe.

One embodiment of a sub-routine (e.g., of the CR) that may be activated during the process 992 to determine whether electrical contact between the probe and the contact point on the sample has been made includes programming to instruct the corresponding positioner control device and/or the CPBD to implement a procedure that obtains information indicative of any electrical contact between the probe tips and the sample. Such procedures may include, among others: (1) positioning two probes on a single contact point; (2) moving probes to share a contact to assure ohmic contact; (3) employing split probe contacts; (4) reversing probes and/or polarity; (5) current sensing; (6) conductance; and (7) changes in secondary electron emission (voltage contrast).

For example, positioning two probes on a single contact point may comprise dropping two probes onto the same contact point and determining whether there is ohmic contact between the two probes. Ohmic contact between the two probes can be indicative of the existence of ohmic contact between either of the two probes and the contact point on the sample.

Figure 14:
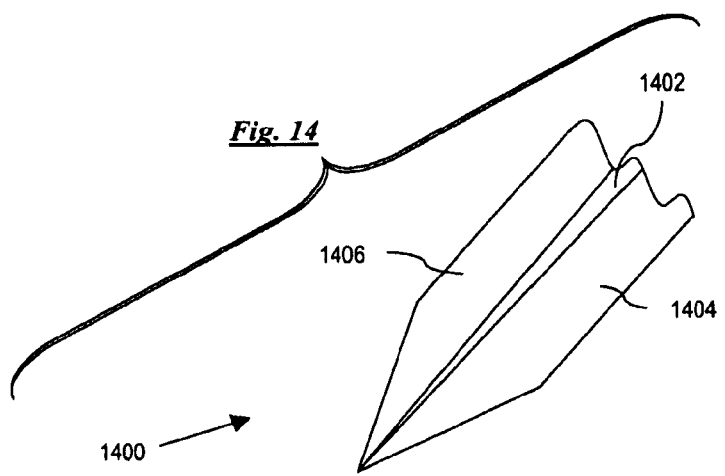
FIG. 14 is a perspective view of at least a portion of one embodiment of apparatus according to aspects of the present disclosure.

A perspective view of an example of a split probe 1400 is illustrated in FIG. 14. The exemplary split probe 1400 employs a probe having a dielectric layer 1402 separating the probe 1400 into "halves" 1404 and 1406. Upon making physical contact between the split probe 1400 and the sample, the detection of ohmic contact between the two "halves" 1404 and 1406 can indicate ohmic contact between the split probe 1400 and the sample contact point.

Reversing probes and/or the polarity or probes to determine whether electrical contact has been made between the probe tips and the contact points can involve making physical contact between each of the two probes and the sample contact point, then: (1) switching the probes; or (2) switching the polarities of each of the probes. Changes in secondary electron emission (voltage contrast) generally involve putting the tip at a certain voltage and determining whether the signal will increase or decrease when the tip makes contact with the contact point. This procedure requires both physical and electrical contact, and thus, if employed, there is no need to execute the sub-routine for determining physical contact. Conductance and current sensing are similar procedures each requiring physical and electrical contact. Thus, if one of these is employed, there is no need to execute the sub-routine for determining physical contact.

Each of the foregoing procedures for determining electrical probe-sample contact may be implemented as one or more partially or substantially automated processes, such as within the APS. Where implemented as one or more semi-automated processes, they may be performed outside of the APS and subsequently reintroduced into the APS upon communications confirming that electrical contact has been made. Depending on the sub-routine executed, the positioner control device or the CPBD may be responsible for sending the communication to the CR that electrical contact has been made.

Figures 12A, 12B, 12C:
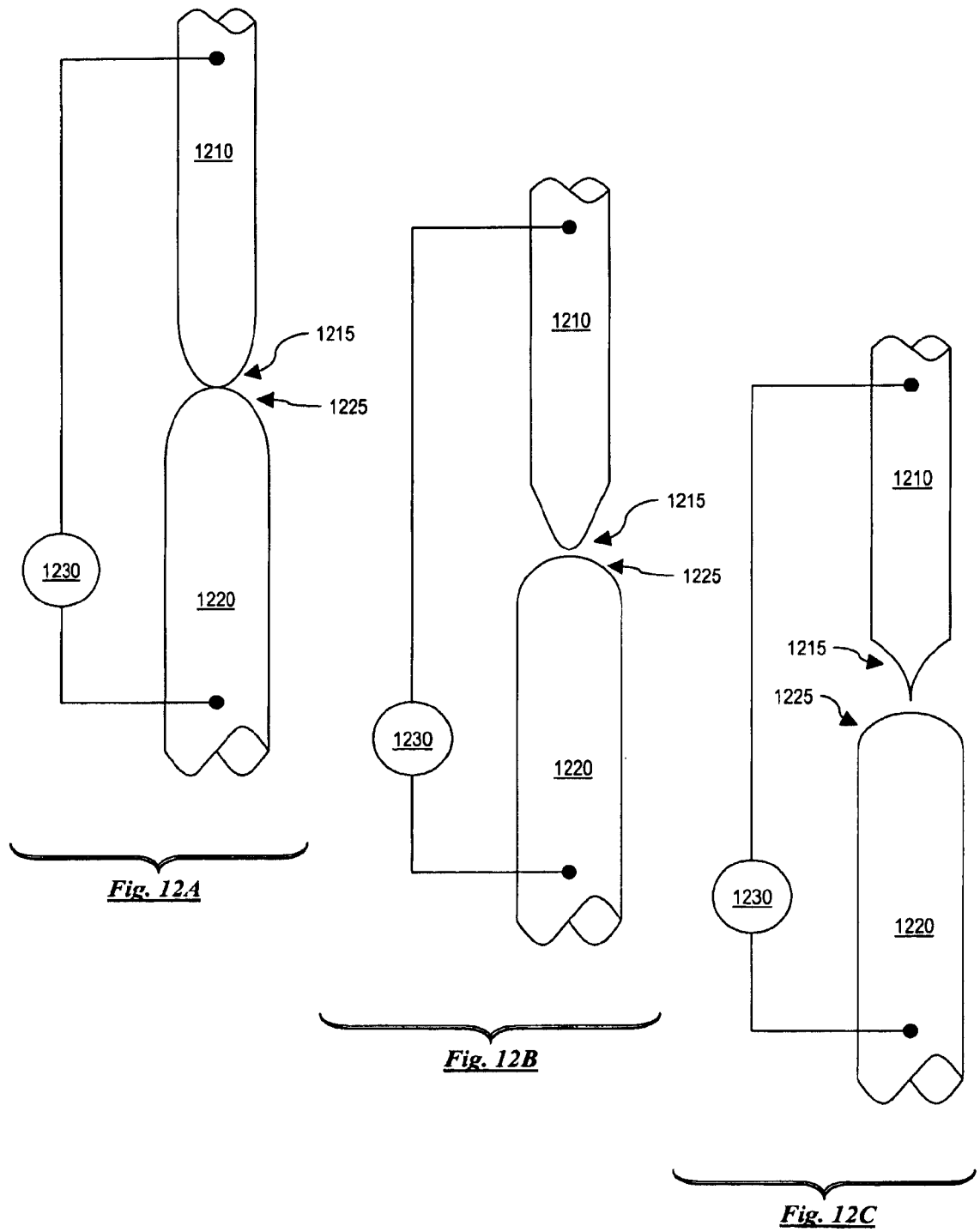
FIGS. 12A-12C are schematic views of various stages of at least a portion of one embodiment of a method according to aspects of the present disclosure.

Referring to FIGS. 12A-12C, collectively, illustrated are schematic views of at least a portion of a probe 1210 during various stages of a probe preparation process according to aspects of the present disclosure. The composition of the probe 1210 may be substantially metallic. The process depicted in FIGS. 12A-12C may be employed to sharpen the probe 1210, such as to sharpen the tip 1215 of the probe 1210. Additionally, or alternatively, the process depicted in FIGS. 12A-12C may be employed to clean the probe 1210 and/or probe tip 1215. However, for the sake of simplicity, the process depicted in FIGS. 12A-12C may be referred to herein as a probe sharpening process. The process depicted in FIGS. 12A-12C may also be substantially similar to the ETP described above, and may be employed to process solid probes (as in the embodiments of FIGS. 12A-12C) or split probes, among others.

FIG. 12A depicts an initial or intermediate stage of the sharpening process. An additional probe 1220 is employed in the depicted process, where the probe 1210 to be sharpened may have a smaller diameter than the probe 1220, may be thinner than the probe 1220, or may otherwise have substantially smaller dimensions relative to the probe 1220, including cross-sectional dimensions and length dimensions. Also, although depicted in FIGS. 12A-12C as being substantially cylindrical, one or both of the probes 1210, 1220 may not be substantially cylindrical or otherwise have a substantially non-circular cross-sectional shape, such as a substantially square or rectangular shape, or an asymmetric shape, among others. In the illustrated embodiment, the probe 1210 initially has a diameter that is about 25% less than the diameter of the probe 1220. Of course, the relative diameters of the probes 1210, 1220 may vary from the illustrated embodiment within the scope of the present disclosure.

As shown in FIG. 12A, the probes 1210, 1220 may be placed in contact to close an electrical loop with a voltage, current or thermal energy source 1230. In other embodiments, however, the probes 1210, 1220 may merely be in close relative proximity but may not be in physical contact with one another.

FIG. 12B depicts a subsequent stage of the sharpening process relative to the stage depicted in FIG. 12A, and in which the tips 1215, 1225 of the probes 1210, 1220, respectively, have been heated to and maintained at an elevated temperature for a sufficient period of time that a portion of the metal forming the probe tip 1215 has dislodged, possibly re-depositing on the probe tip 1225. Thus, for example, the probe tip 1215 has narrowed, while the probe tip 1225 has increased in size.

FIG. 12C depicts a subsequent stage of the sharpening process relative to the stage depicted in FIG. 12B, and in which the tips 1215, 1225 have been maintained at an elevated temperature for a sufficient period of time that an additional amount of metal has dislodged from the probe tip 1215 and possibly re-deposited on the probe tip 1225. Consequently, the probe tip 1215 may be substantially sharpened relative to its status depicted in FIGS. 12A and 12B. The probe tip 1225 may have also increased in size relative to its size depicted in FIGS. 12A and 12B.

Although not limited within the scope of the present disclosure, the elevated temperature at which the probe tips 1215, 1225 are maintained during the probe tip sharpening process described above may range between about 600° C. and about 4000° C. In one embodiment, an elevated probe tip temperature within this range and others may result from resistive heating, such as that which may result from applying across the probe tips 1215, 1225 a voltage ranging between about 1 volt and about 500 volts and/or a current ranging between about 100 nanoamps and about 10 microamps. However, the scope of the present disclosure is not limited to such an embodiment.

The elevated temperature at which the probe tips 1215, 1225 are maintained may also vary between the probe tips 1215, 1225. For example, the elevated temperature at which the probe tip 1215 is maintained may be more or less than the elevated temperature at which the probe tip 1225 is maintained. Additionally, the period of time during which either or both of the probe tips 1215, 1225 may be maintained may range between about 1 second and about 30 seconds. However, this period of time may be substantially less than 1 second, including embodiments effecting a substantially instantaneous metal transfer.

Figure 13A:
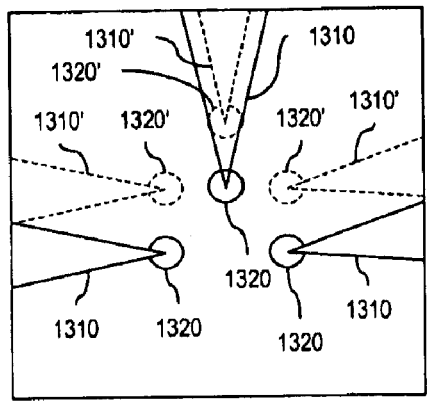
FIGS. 13A-13C are representations of shifting in images generated by a charged particle beam device according to aspects of the present disclosure.
Figure 13B:
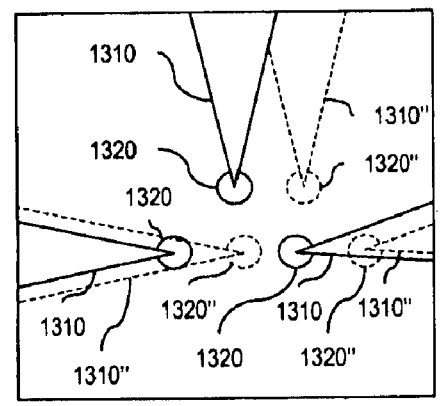
Figure 13C:
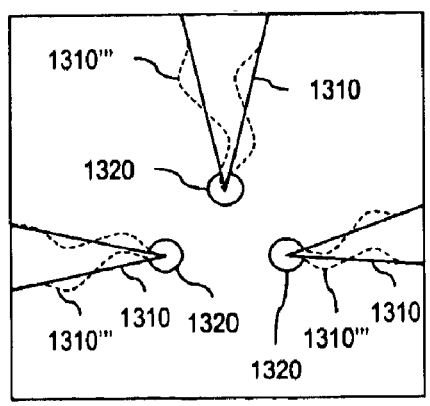

Referring to FIGS. 13A-13C, collectively, illustrated are representations of images 1301-1303 that may each be created with a CPBD according to aspects of the present disclosure, such as those images which may be created when employing an SEM according to one or more partially or substantially automated processes described above. The images 1301-1303 each depict a plurality of probes 1310 that are each positioned over or contacting a corresponding contact point or other feature 1320 of a sample 1330 being investigated within the CPBD.

When investigating a sample in a CPBD, such as employing one or more probes to perform electrical measurement or detection of a characteristic of a sample or sample feature, video rate images of the probes and/or sample can reveal useful information regarding the electrical signal(s) entering and exiting the probes and/or sample. In some situations, an image may shift vertically relative to the CPBD image display device, as depicted in FIG. 13A. In other situations, an image may shift horizontally relative to the CPBD image display device, as depicted in FIG. 13B. In still further situations, an image may oscillate and/or become blurry, as depicted in FIG. 13C. Moreover, these situations may overlap. For example, an image may shift vertically and horizontally, resulting in a diagonal shift having both vertical and horizontal components relative to the CPBD image display device, and an oscillating or blurred image may also shift vertically, horizontally or diagonally relative to the CPBD image display device.

A vertical image shift may at least partially result from electrical bias inherent to the sample investigation, such as when a sample is being investigated in a "power-on" or operational mode relative to when the same sample is being investigated in a substantially identical manner but where the sample is passive, "powered-off" or otherwise unbiased (with the possible exception of any bias resulting from incidence of the CPB of the CPBD). One such example is shown in FIG. 13A, which depicts vertically shifted probes 1310' and contact points 1320' relative to the initially displayed probes 1310 and contact points 1320.

A horizontal image shift may at least partially result from electrical current inherent to the sample investigation, such as when an electrical current is introduced onto a sample or one or more probes, in contrast to when the sample and probes are electrically static (with the possible exception of any bias resulting from incidence of the CPB of the CPBD). One such scenario may be during the above-described probe-current imaging, where the current introduced into the probes may cause the horizontal CPBD image shift in a similar manner to current passed through a semiconductor device, silicon chip or other device being tested. An example of such scenario is shown in FIG. 13B, which depicts horizontally shifted probes 1310" and contact points 1320" relative to the initially displayed probes 1310 and contact points 1320.

An oscillation or blurring may at least partially result from electrical noise resident in the CPBD chamber or control lines, the sample, the probes, and/or other locations. One such example is shown in FIG. 13C, which depicts horizontally shifted probes 1310''' relative to the initially displayed probes 1310.

Images may also exhibit large jumps, possibly about equal to the width of the display screen, when switching electrical measurement scales, or when bias or current abruptly starts or stops. Combinations of motion may also be exhibited. For example, an image may move diagonally across the display screen. Such motion can indicate changing bias/current.

Manual, partially automated and/or substantially automated detection and/or measurement (e.g., shift quantification or shift-distance) of such image shifting and/or motion may be employed alone or in combination with aspects of other methods and procedures described herein. For example, partially or substantially automated vision or detection of an image or image shift at video rates may be employed to gauge the quality of contact between a probe and a sample contact point. Such image shift and/or motion may also be employed to detect and/or measure electrical response, such as the response of a device or circuit in a sample being investigated in a CPBD. Of course, many other characteristics described above or otherwise within the scope of the present disclosure may also be measured and/or detected by processes employing or complimented by processes for detecting and/or measuring image shift and/or motion according to aspects of the present disclosure. In one embodiment, image shift and/or motion data may be collected and logged, possibly analyzed to determine relationships between image behavior, sample characteristics and/or characteristic measurement parameters. For example, the distance that an image may shift in response to current flowing through a probe may be correlated to the magnitude of the current. Consequently, this correlation may be employed to confirm connectivity, contact between the probe and another object, conductivity of the probe, etc.

Thus, the present disclosure introduces an apparatus including a positioner controller configured to control manipulation of: (1) a device under test (DUT) within a charged particle beam device (CPBD); and (2) a probe employed to examine a characteristic of the DUT within the CPBD. The apparatus may also include a measurer. Control of the positioner controller and the measurer may be partially or substantially automated. One embodiment of such apparatus also includes a manipulation platform, which may also be partially or substantially automated. The manipulation platform may include a base and a stage coupled to the base and configured to receive a sample to be examined. The manipulation platform may also include a plurality of manipulator module interfaces each coupled to the base and configured to receive a corresponding one of a plurality of manipulator modules each configured to manipulate at least one of a probe and the sample received by the stage. The manipulation platform may also include an interface configured to transfer control and status information between the plurality of manipulator module interfaces and at least one of the measurer and the positioner controller.

Other embodiments may include one more of: (1) a charged particle beam device (CPBD) in which a sample to be measured is positioned; (2) a positioner control device communicatively coupled to the CPBD and operable to individually manipulate each of a plurality of probes into contact with one of a plurality of contact points on the sample; (3) a measuring device communicatively coupled to the CPBD and the positioner control device and operable to perform one of a measurement and a detection of a characteristic associated with one of the plurality of contact points; and (4) a control routine operable to provide communications to at least one of the CPBD, the positioner control device and the measuring device.

The present disclosure also introduces methods which can include exposing one of several probes to a CPB of a CPBD. Such method may also include examining a current in at least one of the probes, as the current may indicate which of the probes is exposed to the CPB.

The present disclosure also introduces methods which can include introducing a generated signal current to one of a plurality of probes positioned in a CPBD, and exposing each of the probes to a CPB of the CPBD. In an image created by the CPBD, the probe to which the generated signal current is introduced is identified based on its unique representation relative to representations of other probes in the image.

The present disclosure also introduces methods which can include imaging a DUT and a plurality of probes with a CPBD. Individual locations of each of the probes is determined based on beam induced probe current images. Target locations and/or probe relocation paths each corresponding to one of the probes may be retrieved from a software interface input or user input. Scans approximating the relocation paths may be generated, and each of the probes may be moved towards its target location based substantially on its relocation path. Beam induced currents corresponding to the probes may then be analyzed, and positioning errors and correctional drive signals may also be determined.

The present disclosure also introduces methods which can include positioning a probe over a DUT located within a CPBD, translating the probe toward a contact point on the DUT, and iteratively repeating the positioning and the translating until touchdown of the probe on the contact point is determined. The quality of the electrical contact between the probe and the contact point is then assessed, and an electrical measurement is performed with the probe if the assessed quality of the electrical contact falls within a predetermined acceptance criteria.

The present disclosure also introduces methods which can include including collecting data from a CPBD regarding a characteristic of a sample being examined within a chamber of the CPBD, storing the collected data, processing the stored data, and transferring electronically the processed data to an apparatus configured to electronically communicate with the CPBD. At least one of the collecting, storing, processing and transferring may be substantially automated. The apparatus configured to electronically communicate with the CPBD may be a master controller, such as those described above. A master controller may be or include one or more devices and/or units, whether hardware and/or software, which may be configured to control the overall sequencing of application logic. For example, a master controller may determine and execute a particular order of operations for a given process that is being engaged by a user or machine, or a set of such processes.

The present disclosure also introduces methods which can include positioning a first probe tip proximate a second probe tip. At least one of the probe tips is heated such that a portion of probe material forming that probe tip dislodges to sharpen the probe tip.

The present disclosure also introduces methods which can include examining a shift and/or motion of an image relative to a CPBD device on which the image is displayed. The status and/or change in status of an electrical characteristic of at least one of an environment of a CPBD chamber, a sample located with the CPBD chamber, and a probe located within the CPBD chamber may then be determined based on the image shift and/or motion.

Although embodiments of the present disclosure have been described in detail, those skilled in the art should understand that they can make various changes, substitutions and alterations herein without departing from the spirit and scope of the present disclosure.

What is claimed is:

1. A method, comprising:
    transferring a probe to a chamber of a charged particle beam device (CPBD);
    establishing contact between the probe and a contact point of a device under test (DUT) positioned within the CPBD chamber;
    measuring a characteristic of the DUT while the probe is contacting the DUT contact point;
    contacting a first probe tip of the probe with a second probe tip of another probe within the CPBD chamber, prior to establishing contact between the probe and the DUT contact point; and
    heating the first probe tip such that a portion of material forming the first probe tip dislodges to sharpen the first probe tip, prior to establishing contact between the probe and the DUT contact point;
    wherein at least one of the transferring, the establishing and the measuring is via substantial automation.

2. The method of claim 1 wherein each of the transferring, the establishing and the measuring is via substantial automation.

3. The method of claim 1 further comprising mechanically coupling the probe and a probe positioner via substantial automation prior to transferring the probe to the CPBD chamber.

4. The method of claim 1 further comprising at least one of:
    positioning the DUT within the CPBD chamber via substantial automation prior to establishing contact between the probe and the CPBD;
    de-processing the DUT via substantial automation prior to establishing contact between the probe and the DUT contact point;
    preparing the DUT via substantial automation prior to establishing contact between the probe and the DUT contact point;
    assessing via substantial automation an electrical quality of contact between the probe and the DUT contact point after establishing the contact;
    conditioning the probe via substantial automation if the assessed electrical quality does not fall within predetermined acceptance criteria; and
    retracting the DUT from the CPBD chamber via substantial automation after measuring the DUT characteristic.

5. The method of claim 1 further comprising at least one of preparing, conditioning and characterizing the probe via substantial automation within the CPBD chamber.

6. The method of claim 1 further comprising storing the probe within the CPBD chamber via substantial automation.

7. The method of claim 1 further comprising exchanging the probe with an additional probe positioned within the CPBD chamber, wherein the exchanging is via substantial automation.

8. The method of claim 1 wherein the probe is one of first and second probes positioned in the CPBD chamber, and wherein measuring the DUT characteristic includes:
    exposing one of the first and second probes to a charged particle beam (CPB) of the CPBD; and
    examining a current in at least one of the first and second probes, wherein the current is indicative of which of the first and second probes is exposed to the CPB.

9. The method of claim 1 wherein the at least one of the transferring, the establishing and the measuring via substantial automation includes controlling a positioner controller to position at least one of the DUT and the probe within the CPBD chamber.

10. The method of claim 1 wherein transferring the probe to the CPBD chamber includes storing at least one end-effector in a storage structure that is positioned within the CPBD chamber.

11. The method of claim 1 wherein establishing contact between the probe and the contact point of the DUT comprises positioning control by at least partial automation of at least one of:
    orientation of the DUT within the CPBD chamber;
    orientation of the probe within the CPBD chamber; and
    relative orientation of the probe and the DUT within the CPBD chamber.

12. The method of claim 1 further comprising, after measuring the characteristic:

collecting data regarding the characteristic;
storing the collected data;
processing the stored data; and
transferring electronically the processed data to an apparatus configured to electronically communicate with the CPBD;
wherein at least one of the collecting, storing, processing and transferring is via substantial automation.

13. The method of claim 1 wherein measuring the characteristic includes:
examining at least one of a shift and motion of an image of at least one of the probe and the DUT; and
determining at least one of a status and a change in status of an electrical characteristic of at least one of an environment of the CPBD chamber, the DUT located with the CPBD chamber, and the probe located within the CPBD chamber, wherein the determining is based on the at least one of the image shift and motion.

14. The method of claim 1 wherein the at least one of the transferring, the establishing and the measuring via substantial automation includes controlling a positioner controller to position at least one of the DUT and the probe within the CPBD chamber.

15. A method, comprising:
transferring a probe to a chamber of a charged particle beam device (CPBD);
establishing contact between the probe and a contact point of a device under test (DUT) positioned within the CPBD chamber; and
measuring a characteristic of the DUT while the probe is contacting the DUT contact point;
wherein at least one of the transferring, the establishing and the measuring is via substantial automation;
wherein transferring the probe to the CPBD chamber includes storing at least one end-effector in a storage structure that is positioned within the CPBD chamber; and
wherein the probe is an examination probe, wherein the end-effector includes the examination probe and an assembly probe extending in opposing directions, and wherein the assembly probe is configured to couple with a positioner.

16. The method of claim 15 further comprising establishing a connection between the assembly probe and a corresponding socket of the positioner.

17. The method of claim 15 wherein each of the transferring, the establishing and the measuring is via substantial automation.

18. The method of claim 15 further comprising mechanically coupling the probe and a probe positioner prior to transferring the probe to the CPBD chamber.

19. The method of claim 15 further comprising at least one of:
positioning the DUT within the CPBD chamber via substantial automation prior to establishing contact between the probe and the CPBD;
de-processing the DUT via substantial automation prior to establishing contact between the probe and the DUT contact point;
preparing the DUT via substantial automation prior to establishing contact between the probe and the DUT contact point;
assessing via substantial automation an electrical quality of contact between the probe and the DUT contact point after establishing the contact;
conditioning the probe via substantial automation if the assessed electrical quality does not fall within predetermined acceptance criteria; and
retracting the DUT from the CPBD chamber via substantial automation after measuring the DUT characteristic.

20. The method of claim 15 further comprising at least one of preparing, conditioning and characterizing the probe via substantial automation within the CPBD chamber.

21. The method of claim 15 further comprising storing the probe within the CPBD chamber.

22. The method of claim 15 further comprising exchanging the probe with an additional probe positioned within the CPBD chamber.

23. The method of claim 15 wherein the probe is one of first and second probes positioned in the CPBD chamber, and wherein measuring the DUT characteristic includes:
exposing one of the first and second probes to a charged particle beam (CPB) of the CPBD; and
examining a current in at least one of the first and second probes, wherein the current is indicative of which of the first and second probes is exposed to the CPB.

24. The method of claim 15 further comprising, after measuring the characteristic:
collecting data regarding the characteristic;
storing the collected data;
processing the stored data; and
transferring electronically the processed data to an apparatus configured to electronically communicate with the CPBD;
wherein at least one of the collecting, storing, processing and transferring is via substantial automation.

25. The method of claim 15 wherein measuring the characteristic includes:
examining at least one of a shift and motion of an image of at least one of the probe and the DUT; and
determining at least one of a status and a change in status of an electrical characteristic of at least one of an environment of the CPBD chamber, the DUT located with the CPBD chamber, and the probe located within the CPBD chamber, wherein the determining is based on the at least one of the image shift and motion.

26. The method of claim 15 wherein transferring the probe to the CPBD chamber includes storing at least one end-effector in a storage structure that is positioned within the CPBD chamber.

27. The method of claim 15 wherein establishing contact between the probe and the contact point of the DUT comprises positioning control by at least partial automation of at least one of:
orientation of the DUT within the CPBD chamber;
orientation of the probe within the CPBD chamber; and
relative orientation of the probe and the DUT within the CPBD chamber.

* * * * *